(12) United States Patent
Fritzberg

(10) Patent No.: US 7,385,042 B2
(45) Date of Patent: *Jun. 10, 2008

(54) THERAPEUTIC AND DIAGNOSTIC COMPOUNDS, COMPOSITIONS, AND METHODS

(75) Inventor: Alan R. Fritzberg, Olga, WA (US)

(73) Assignee: Poniard Pharmaceuticals, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/486,338

(22) Filed: Jul. 13, 2006

(65) Prior Publication Data

US 2006/0251578 A1   Nov. 9, 2006

Related U.S. Application Data

(63) Continuation of application No. 10/615,484, filed on Jul. 8, 2003, now Pat. No. 7,115,720, which is a continuation of application No. PCT/US02/00629, filed on Jan. 8, 2002.

(60) Provisional application No. 60/260,349, filed on Jan. 8, 2001.

(51) Int. Cl.
  *C07F 13/00* (2006.01)
(52) U.S. Cl. .................. 534/14; 534/10; 424/1.11; 424/1.65
(58) Field of Classification Search .............. 424/1.11, 424/1.65, 9.1, 1.81, 1.85, 1.37; 206/223, 206/569, 570; 534/7, 10–16; 546/1; 540/1, 540/450; 514/156
See application file for complete search history.

(56) References Cited

U.S. PATENT DOCUMENTS

| | | | |
|---|---|---|---|
| 3,032,584 A | 5/1962 | Bergel et al. | |
| 3,032,585 A | 5/1962 | Bergel et al. | |
| 3,398,198 A | 8/1968 | Kersnar et al. | |
| 3,726,912 A | 4/1973 | McCrary et al. | |
| 3,852,414 A | 12/1974 | Adler et al. | |
| 3,931,396 A | 1/1976 | Bardy et al. | |
| 3,965,254 A | 6/1976 | Tofe et al. | |
| 3,974,268 A | 8/1976 | Subramanian et al. | |
| 3,989,730 A | 11/1976 | Subramanian et al. | |
| 4,017,596 A | 4/1977 | Loberg et al. | |
| 4,058,704 A | 11/1977 | Shimizu | |
| 4,075,314 A | 2/1978 | Wolfangel et al. | |
| 4,104,366 A | 8/1978 | Schmidt-Dunker et al. | |
| 4,187,284 A | 2/1980 | Rolleston et al. | |
| 4,247,534 A * | 1/1981 | Bevan | 424/1.77 |
| 4,399,817 A | 8/1983 | Benedict | |
| 4,508,625 A | 4/1985 | Graham | |
| 4,515,767 A | 5/1985 | Simon et al. | |
| 4,560,548 A | 12/1985 | Simon et al. | |
| 4,606,907 A | 8/1986 | Simon et al. | |
| 4,639,365 A | 1/1987 | Sherry | |
| 4,647,447 A | 3/1987 | Gries et al. | |
| 4,678,667 A | 7/1987 | Meares et al. | |
| 4,707,353 A | 11/1987 | Bugaj et al. | |
| 4,752,464 A | 6/1988 | Lieberman et al. | |
| 4,808,541 A | 2/1989 | Mikola et al. | |
| 4,853,209 A | 8/1989 | Kaplan et al. | |
| 4,882,142 A | 11/1989 | Simon et al. | |
| 4,885,363 A | 12/1989 | Tweedle et al. | |
| 4,897,254 A | 1/1990 | Simon et al. | |
| 4,897,255 A | 1/1990 | Fritzberg et al. | |
| 4,898,724 A | 2/1990 | Simon et al. | |
| 4,937,333 A | 6/1990 | Garlich et al. | |
| 4,957,939 A | 9/1990 | Gries et al. | |
| 4,976,950 A | 12/1990 | Simon et al. | |
| 5,059,412 A | 10/1991 | Simon et al. | |
| 5,064,633 A | 11/1991 | Simon et al. | |
| 5,066,478 A | 11/1991 | Simon et al. | |
| 5,089,249 A | 2/1992 | Fritzberg et al. | |
| 5,202,109 A | 4/1993 | Fritzberg et al. | |
| 5,286,497 A | 2/1994 | Hendrickson et al. | |
| 5,300,279 A | 4/1994 | Simon et al. | |
| 5,393,512 A | 2/1995 | Vanderheyden et al. | |
| 5,587,451 A | 12/1996 | Athey et al. | |
| 5,621,001 A | 4/1997 | Canetta et al. | |
| 5,641,803 A | 6/1997 | Canetta et al. | |
| 5,665,761 A | 9/1997 | Canetta et al. | |

(Continued)

FOREIGN PATENT DOCUMENTS

CA    1078731    6/1980

(Continued)

OTHER PUBLICATIONS

"Abstract Book, Annual Congress of the EANM", *European Journal of Nuclear Medicine and Molecular Imaging*, 31, Helsinki, 2004, including abstracts P908, P925-P936, and P946-P952,(2004).

(Continued)

*Primary Examiner*—Dameron L. Jones
(74) *Attorney, Agent, or Firm*—Schwegman, Lundberg & Woessner, P.A.

(57) ABSTRACT

One embodiment provides a composition comprising a) a compound of formula I:

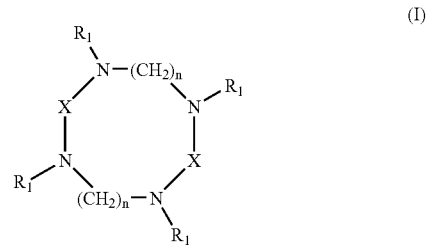

wherein $R_1$, X and n have any of the values described in the specification, or a pharmaceutically acceptable salt thereof; b) a radionuclide; and c) a radioprotectant.

16 Claims, 6 Drawing Sheets

U.S. PATENT DOCUMENTS

| | | | |
|---|---|---|---|
| 5,670,537 A | 9/1997 | Canetta et al. | |
| 5,679,318 A | 10/1997 | Vanderheyden et al. | |
| 5,707,610 A | 1/1998 | Ibsen et al. | |
| 5,708,169 A | 1/1998 | Hester, Jr. et al. | |
| 5,712,275 A | 1/1998 | Van Gestel | |
| 5,714,467 A | 2/1998 | Boman et al. | |
| 5,714,504 A | 2/1998 | Lindberg et al. | |
| 5,714,604 A | 2/1998 | Kiefer | |
| 5,756,472 A | 5/1998 | Liesch et al. | |
| 5,756,505 A | 5/1998 | Nishino et al. | |
| 5,756,685 A | 5/1998 | Fritzberg et al. | |
| 5,756,725 A | 5/1998 | Wilkening et al. | |
| 5,760,063 A | 6/1998 | Lam et al. | |
| 5,762,907 A | 6/1998 | Simon et al. | |
| 5,770,617 A | 6/1998 | LaVoie et al. | |
| 5,773,421 A | 6/1998 | Alder et al. | |
| 5,773,443 A | 6/1998 | Ray et al. | |
| 5,773,696 A | 6/1998 | Liang et al. | |
| 5,783,570 A | 7/1998 | Yokota et al. | |
| 5,786,325 A | 7/1998 | Borromeo et al. | |
| 5,801,172 A | 9/1998 | Clapp-Shapiro et al. | |
| 5,807,854 A | 9/1998 | Bartroli et al. | |
| 5,814,634 A | 9/1998 | Nishino et al. | |
| 5,824,698 A | 10/1998 | Hasler et al. | |
| 5,824,874 A | 10/1998 | Ulbrich et al. | |
| 5,830,855 A | 11/1998 | Takemoto | |
| 5,830,889 A | 11/1998 | Iwata et al. | |
| 5,837,253 A | 11/1998 | Cohen | |
| 5,837,726 A | 11/1998 | Liu et al. | |
| 5,849,956 A | 12/1998 | Koga et al. | |
| 5,854,213 A | 12/1998 | Bouffard | |
| 5,854,280 A | 12/1998 | Gomez et al. | |
| 5,856,347 A | 1/1999 | Hashiguchi et al. | |
| 5,859,032 A | 1/1999 | Nishino et al. | |
| 5,861,430 A | 1/1999 | Markonius | |
| 5,863,773 A | 1/1999 | Gunawardana et al. | |
| 5,866,549 A | 2/1999 | Or et al. | |
| 5,872,249 A | 2/1999 | Park et al. | |
| 5,876,738 A | 3/1999 | Ohno et al. | |
| 5,888,526 A | 3/1999 | Tsubai et al. | |
| 5,888,941 A | 3/1999 | Bartroli et al. | |
| 5,891,890 A | 4/1999 | Nishino et al. | |
| 5,908,862 A | 6/1999 | Wai Lee et al. | |
| 5,910,498 A | 6/1999 | Yazaki et al. | |
| 5,917,084 A | 6/1999 | Jiang | |
| 5,919,438 A | 7/1999 | Saint-Leger | |
| 5,919,925 A | 7/1999 | Burton et al. | |
| 6,005,083 A | 12/1999 | Kasina | |
| 6,177,551 B1 | 1/2001 | Kasina | |
| 6,187,910 B1 | 2/2001 | Kasina | |
| 6,241,961 B1 | 6/2001 | Benes et al. | |
| 6,528,627 B1 | 3/2003 | Kasina | |
| 6,767,531 B2 | 7/2004 | Fritzberg et al. | |
| 7,115,720 B2 * | 10/2006 | Fritzberg | 534/14 |
| 2002/0176814 A1 | 11/2002 | Fritzberg et al. | |
| 2003/0118508 A1 | 6/2003 | Simon et al. | |
| 2003/0158393 A1 | 8/2003 | Kasina | |
| 2004/0096393 A1 | 5/2004 | Fritzberg | |
| 2004/0126317 A1 | 7/2004 | Fritzberg | |
| 2005/0063905 A1 | 3/2005 | Fritzberg et al. | |
| 2005/0129667 A1 | 6/2005 | Fritzberg et al. | |
| 2005/0238578 A1 | 10/2005 | Fritzberg et al. | |

FOREIGN PATENT DOCUMENTS

| | | |
|---|---|---|
| EP | 0164843 | 12/1985 |
| EP | 0210043 | 1/1987 |
| EP | 0232751 | 8/1987 |
| EP | 0255471 | 2/1988 |
| EP | 0258616 | 3/1988 |
| EP | 0287465 | 10/1988 |
| EP | 0374501 | 6/1990 |
| EP | 0382582 | 8/1990 |
| EP | 0408701 | 1/1991 |
| EP | 0411941 | 2/1991 |
| EP | 0455380 | 11/1991 |
| EP | 0698029 | 2/1996 |
| EP | 0972528 | 1/2000 |
| FR | 2230374 | 12/1974 |
| WO | WO-84/03698 | 9/1984 |
| WO | WO-90/06776 | 6/1990 |
| WO | WO-9006776 | 6/1990 |
| WO | WO-91/16075 | 10/1991 |
| WO | WO-9116075 | 10/1991 |
| WO | WO-9325240 | 12/1993 |
| WO | WO-94/26753 | 11/1994 |
| WO | WO-95/10940 | 4/1995 |
| WO | WO-98/43678 | 10/1998 |
| WO | WO-0076556 | 12/2000 |
| WO | WO-0191806 | 12/2001 |
| WO | WO-02/062398 | 8/2002 |

OTHER PUBLICATIONS

"Bone Cancer Therapy Project Funding Awarded to Brookhaven National Laboratory for Diatide-Licensed Product", DISTRIBUTION: Business Editors and Health/Medical Writers,(1999).

"Breast Cancer; Genitourinary Cancer; Multiple Myeloma", *Annotated Guide to Cancer Chemotherapeutic Regimens 1999/2000*, Oncology Special Edition,13-14; 17-18; 32.

"Chaper III: Chemotherapy Regimens in Adults", *In Cancer Chemotherapy Pocket Guide*, Robert J. Ignoffo, Editor,(1998),248-255; 338-341.

"Manufacture of Triethylene Tetramine", *Research Disclosure*, 315, No. 31591,(1990),595.

"Multiple Myeloma", *In Clinical Oncology, A Multidisciplinary Approach for Physicians and Students, 7th Edition*, Phillip Rubin, Editor,(1993),239-244.

"NeoRx Updates Skeletal Targeted Radiotherapy (STR) Phase I/II Trail Data", *NeoRx Press Release*, (May 7, 2001).

"NeoRx's Multiple Myeloma Study with Targeted Radiotherapy to be Updated at ASH—Recent Thaliomide Results Heighten Interest in New Multiple Myeloma Therapies", *NeoRx Press Release*, (Nov. 30, 1999).

"NeoRx's Targeted Radiotherapy Achieves Complete Responses with Excellent Safety in Multiple Myeloma Patients", *NeoRx Press Release*, (Dec. 7, 1999).

"Phase I/II Interim Data on NeoRx's STR Product in Multiple Myeloma", *NeoRx Press Release*, (1999).

Abrams, Paul, "High Dose Targeted Radiation to Bone and Bone Metastases", *CaP CURE Meeting*, Lake Tahoe, NV, (2000),2 pages.

Alexanian, R , et al., "Impact of Complete Remission with Intensive Therapy in Patients with Responsive Multiple Myeloma", *British Journal of Hematology*, 27(10), (2001), 1037-1043.

Anderson, et al., "High-Dose Samarium-153 Ethylene Diamine Tetramethylene Phosphonate: Low Toxicity of Skeletal Irradiation in Patients with Osteosarcoma and Bone Metastases", *Journal of Clinical Oncology*, 20, (2002),189-196.

Ando, A , et al., "177Lu-EDTMP: A Potential Therapeutic Bone Agent", *Nucl. Med. Commun*, 19(6), (1998),587-591.

Appelbaum, F R., et al., "Chronic and Acute Leukemias in Adults", *The Role of Marrow Transplantation in the Treatment of Leukemia*, Martinus Nijhoff Publisjers, Boston. C.D. Bloomfield, editor,(1985),229-262.

Appelbaum, F. R., et al., "Specific Marrow Ablation Before Marrow Transplantation Using an Aminophosphonic Acid Conjugate 166Ho-EDTMP", *Blood*, 80, (1992),1608-1613.

Bardies, M , et al., "Computational Methods in Radionuclide Dosimetry", *Physics in Medicine and Biology*, 41, (1996),1941-1955.

Barlogie, B , "Prognostic Factors with High-Dose Melphalan for Refractory Multiple Myeloma.", *Blood*, 72(6), (Dec. 1988),2015-2019.

Bataille, R., et al., "Multiple Myeloma", *New England Journal of Medicine*, 336, (1997),1657-1664.

Bayouth, J. E., et al., "Dosimetry Considerations of Bone-Seeking Radionuclides for Marrow Ablation", *Medical Physics*, 20(4), (Jul.-Aug. 1993),1089-1096.

Bayouth, J. E., et al., "Pharmacokinetics, Dosimetry and Toxicity of Homium-166-DOTMP for Bone Marrow Ablation in Multiple Myeloma", *Journal of Nuclear Medicine*, 36(5), (May 1995),730-737.

Bayouth, J. E., et al., "Radiation Dose Distribution Within the Bone Marrow of Patients Recieving Holmium-166-Labeled-Phosphonate for Marrow Ablation", *Medical Physics*, 22(6), (Jun. 1995),743-753.

Bearman, et al., "Regimen-related Toxicity in Patients Undergoing Bone Marrow Transplantation", *Journal of Clinical Oncology*, 6(10), (Oct. 1988),1562-1568.

Beddoe, A H., et al., "Measurements of Trabecular Bone Structure in Man", *Physics in Medicine and Biology*, 21(4), (Jul. 1976),589-607.

Bensinger, et al., "166Ho-DOTMP and High-Dose Melphalan before Autologous Peripheral Blood Stem Cell Transplantation in Patients with Multiple Myeloma", Abstract P287; IXth International Workshop on Multiple Myeloma,(2003).

Bensinger, B., et al., "166Holmium-DOTMP Plus Standard High Dose Chemotherapy (HDC) with Autologous Transplant Produce High Rates of Complete Remission (CR) in Multiple Myeloma (MM) Patients: An Updated Report of a Phase I/II Study", *Proceedings of the American Society of Clinical Oncology*, 20, Abstract No. 18,(2001),5a.

Bensinger, W., et al., "Phase I/II Study of 166Holmium-DOTMP in Combination with Melphalan +/− Total Body Irradiation (TBI) with Autologous Peripheral Blood Stem Cell Transplant (PBSCT) for Patients with Multiple Myeloma", *Proceedings of the American Society of Clinical Oncology 2000*, 19, Abstract No. 26,(2000),9a.

Bensinger, et al., "Skeletal Targeted Radiotherapy (STR) with 166Ho-DOTMP plus Melphalan and Autologous Stem Cell Transplant (ASCT) in Multiple Myeloma(MM)", *Meeting Proccedings of ASCO*, 22, ASCO Annual Meeting, May 2003; Abstract No. 3346,(2003),833.

Bigler, R., et al., "Skeletal Distribution of Mineralized Bone Tissue in Humans", *Health Physics*, 31, (1976),213-218.

Boussiotis, V A., et al., "Bone Marrow Transplantation for Low-grade Lymphoma and Chronic Lymphocytic Leukemia", *Semin Hematol*, 36, (1999),209-216.

Breitz, H., "Dosimetry in a Myeloablative Setting", Annual Society of Nuclear Medicine Meeting, Continuing Education Course,(2001).

Breitz, H., et al., "Dosimetry in Myeloblative Setting", *Cancer Biother. Radiopharm.*, 17(1), (2002),119-128.

Breitz, et al., "Dosimetry of High Dose Skeletal Targeted Radiotherapy (STR) with 166-Ho-DOTMP", *Cancer Biotherapy and Radiopharmaceuticals*, 18, (2003),225-230.

Breitz, H., et al., "Dosimetry of High Dose Skeletal Targeted Radiotherapy wit Ho-166 DOTMP", *Presentation at VIIth International Radiopharmaceutical Dosimetry Symposium*, (2002).

Breitz, H., et al., "Multiple Myeloma: Skeletal Targeted Radiotherapy with 166-Ho-DOTMP for Treatment of Multiple Myeloma", *Presented at "Targeted Radionuclide Therapy"*, (2002).

Breitz, H., "Quantitative Dosimetry Workup in a Myeloablative Setting", Presentation at the 48th Annual Society for Nuclear Medicine Meeting,(2001).

Champlin, R., et al., "166Holmium-DOTMP in Combination with Melphalan with or without Total Body Irradiation as a Preparative Regimen for Autologous Stem Cell Transplant (ASCT) for Patients with Multiple Myeloma (MM)", *Blood*, 94(10), American Society of Hematology, Abstract No. 3133,(1999),709a.

Champlin, R., et al., "Bone Marrow Transplantation for Acute Leukemia: Recent Advances and Comparison with Alternative Therapies", *Seminars in Hematology*, 24, (1987),55-67.

Champlin, R., et al., "Holmium-166 DOTMP, A Bone Seeking Radiochelate for Selective Marrow Radiotherapy with Bone Marrow Transplantation (BMT) for Multiple Myeloma", *Experimental Hematology*, 21, Abstracts, 22nd Annual Meeting of the International Society for Experimental Hematology, Rotterdam, The Netherlands, Abstract No. 393,(1993),1117.

Champlin, R., et al., "Holmium-166 DOTMP, A Bone Seeking Radiochelate For Selective Marrow Radiotherapy with Bone Marrow Transplantation (BMT) for Multiple Myeloma", *Blood*, 82, Abstracts, American Society of Hematology Thirty-Fifth Annual Meeting, St. Louis, MO, Abstract No. 1051,(1993),266a.

Champlin, R., et al., "Phase I/II Study of Targeted Radiotherapy Using 166Ho-DOTMP with Melphalan and Peripheral Blood Stem Cell Transplant for Multiple Myeloma", A slide presentation, International Society of Experimental Hematology,(2000).

Champlin, R., et al., "Role of Bone Marrow Transplantation in the Treatment of Hematologic Malignancies and Solid Tumors: Critical Review of Syngeneic, Autologous, and Allogeneic Transplants.", *Cancer Treatment Reports*, 68, (1984),145-161.

Champlin, R., et al., "Two Phase I/II Studies of 166Holmium-DOTMP in Combination with Melphalan With or Without Total Body Irradiation as a Preparative Regimen for Autologous Stem Cell Transplant (PBSCT) for Patients with Multiple Myeloma", *Experimental Hematology*, 27(7), Abstract No. 196, Program and Abstracts, 28th Annual Meeting of the International Society for Experimental Hematology, Monte Carlo, Monaco.,(1999),88.

Cleynhens, et al., "99mTc-EC-AMDP, a Bone Agent with Rapid Clearance from Soft Tissue", *Technetium, Rhenium and Other Metals in Chemistry and Nuclear Medicine*, 5, (1999),605-609.

Cohen, et al., "Bisphosphonates and Tetracycline: Experimental Models for Their Evaluation in Calcium-Related Disorders", *Pharmaceutical Research*, 15, (1998),606-613.

Cunningham, D., et al., "High-dose Melphalan for Multiple Myeloma: Long-term Follow-up Data", *Journal of Clinical Oncology*, 12, (1994),764-768.

Dispenzieri, et al., "A Phase I Study of a Conditioning Regimen for Peripheral Stem Cell Transplantation (PBSCT) for Multiple Myeloma (MM): 153Samarium Ethylenediaminetetramethylenephosphonate (153SM-EDMPT) and Melphalan", *Blood*, 96, Abstract 2397,(2000),558a.

Dispenzieri, et al., "A Phase I/II Dose Escalation Study of 153-Samarium EDTMP (153-Sm-EDMTP) with Fixed Dose Melphalan Peripheral Stem Cell Transplantation (PBSCT) for Multiple Myeloma (MM)", *Blood*, 98, Abstract 2855,(2001),682a-683a.

Durrant, Simon, et al., "Sm-153 Lexidronam, Limb Irradiation and Stem Cell Transplantation for the Treatment of Multiple Myeloma", Amer. Soc. Hemeotology Annual Meeting, Orlando, FL.,(2001).

Eary, Janet F., "Samarium-153-EDTMP Biodistribution and Dosimetry Estimation", *The Journal of Nuclear Medicine*, 34, (1993),1031-1036.

Eckerman, K., et al., "Dose Conversion Factors for Marrow and Bone by Skeletal Regions", *Journal of Nuclear Medicine*, 35, (1994),112P.

Eisenhut, M., "Iodine-131-Labeled Diphosphonates for the Palliative Treatment of Bone Metastases: I. Organ Distribution and Kinetics of I-131 BDP3 in Rats", *The Journal of Nuclear Medicine*, 25, (1984),1356-1361.

Eisenhut, et al., "The Influence of Substituents in 99mTc-Benzylidenediphosphonate Complexes on their Organ Distribution in Rats", *Nuklearmedizin*, 23, (1984),119-122.

Firusian, N., et al., "Results of 89Strontium Therapy in Patients with Carcinoma of the Prostate and Incurable Pain from Bone Metastases: A Preliminary Report", *The Journal of Urology*, 116, (1976),764-768.

Fritzberg, Alan R., "Holmium-166 DOTMP for Marrow Ablation: Clinical Studies to Demonstrate Efficacy in Multiple Myeloma", Society of Nuclear Medicine Annual Meeting, St. Louis,(2000).

Fujisaki, et al., "Physicochemical Characterization of Bisphosphonic Carboxyfluorescein for Osteotropic Drug Delivery", *J Pharm Pharm Pharmacol.*, 48, (1996),798-800.

Garlich, J R., et al., "Chemical Considerations of 153Sm-EDTMP, a New Therapeutic Bone Agent", Sixth International Symposium on Radiopharmaceutical Chemistry: Abstracts. Boston, Jun. 29-Jul. 3, 1986. Paper 140,(1986),317-319.

Garlich, J. R., et al., "Chemistry of Novel Macrocyclic Aminophosphonic Acid Chelates of Rare Earth Radionuclides and Their in vivo Biodistribution", *The Journal of Nuclear Medicine*, 34, Abstract Book, Proceedings of the 40th Annual Meeting, Toronto, Ontario, Canada, Abstract No. 1134,(1993),244P.

Geraldes, C F., et al., "Synthesis, Protonation Sequence, and NMR Studies of Polyazamacrocyclic Methylenephosphonates", *Inorganic Chemistry*, 28, (1989),3336-3341.

Giralt, et al., "166Ho-DOTMP Plus Melphalan Followed by Peripheral Blood Stem Cell Transplantation in Patients with Multiple Myeloma: Results of Two Phase I/II Trials", *Blood*, Blood First Edition Paper; DOI 10.1182/2002-10-3250,(2003),1-38.

Giralt, S , et al., "Hemorrhagic Cystitis after Targeted Radiotherapy with Holmium-DOTMP (166HO) for Multiple Myeloma (MM) is Preventable with Bladder Irrigation", *Blood*, 96(11), Abstract No. 1686,(2000).

Giralt, et al., "Long-Term Follow-Up of 83 Patients with Multiple Myeloma (MM) Treated on a Phase I-II Study of Skeletal Targeted Radiotherapy (STR) Using 166Ho-DOTMP Plus Melphalan with or without Total Body Irradiation (TBI) and Autologous Hematopoietic Stem Cell . . . ", *Blood*, 100, 44th Annual Meeting of the American Society of Hematology; Abstract 670,(2002),179a.

Giralt, S , et al., "Preliminary Results of a Phase I/II Study of Multiple Myeloma (MM) Patients Treated with 166Holmium-DOTMP in Combination with High Dose Melphalan +/- Total Body Irradiation (TBI) with Autologous Stem Cell Transplant (ASCT)", *Blood*, 96(11), Abstract No. 2395,(2000).

Giralt, S , et al., "Results of a Phase I/II Trial with 166Ho-DOTMP Plus High Dose Chemotherapy in Patients with Multiple Myeloma", *VIIIth Int'l Multiple Myeloma Proceedings*, Abstract No. S24,(2001),40-41.

Giralt, S , et al., "Two Phase I/II Studies of 166Holmium-DOTMP in Combinatiion with or without TBI as a Preparative Regimen for Autologous Stem Cell Transplant (PBSCT) for Patients with Multiple Myeloma", *VIIth Int'l Multiple Myeloma Workshop*, Abstract No. 033, Meeting Held Sep. 1-5, 1999,(1999),117.

Goeckeler, W F., et al., "Samarium-153 Radiotherapeutic Bone Agents", *Nucl. Med. Biol.*, 13, (1986),479-482.

Goldman, "Good Drug, Bad Luck: Business, Regulatory Issues Can Create Obstacles for Drug Development", *Journal of the National Cancer Institute*, 96, (2004),1573-1574.

Hassfjell, S. P., et al., "212Bi-DOTMP: An Alpha Particle Emitting Bone-Seeking Agent for Targeted Radiotherapy", *Nuclear Medicine and Biology*, 24, (1997).231-237.

Hogan, et al., "Successful Treatment of POEMS Syndrome with Autologous Hematopoietic Progenitor Cell Transplantation", *Bone Marrow Transplantation*, 28, (2001),305-309.

Hsia, C , et al., "Preparation of 113min-DTPMP Bone Scanning Agent and its Prliminary Clinical Application", *Chemical Abstracts*, 95, (1981),305.

Jarvis, et al., "Characterization of the Bisphosphonate Recognition Site on Hydroxyapatite Using Radioligand Binding Techniques with [14C]Citric Acid", *Calcif Tissue Int.*, 52, (1993),372-377.

John, E K., et al., "Formulation Development and Stability of the 166Ho- DOTMP for High Level Dosages-13 A Skeletal Targeted Radiotherapeutic", *Journal of Nuclear Medicine*, 42, Proceedings of the SNM 48th Annual Meeting, No. 1122,(2001),267P.

Kabachnik, I M., et al., "Synthesis and Acid-Base and Complex-Forming Properties of 1,4,7,10—Tetrakis (dihydroxyphosohorylmethyl)—1,4,7,10—tetraazacyclododecane", *Bulletin of the Academy of Sciences of the USSR; Division of Chemical Science*, 33, (1984),777-782.

Kabachnik, M I., et al., "Synthesis and Study of a New Complexone—N,N',N"—Tris-(Dihydroxyphosphorylethyl)—1,4,7—Triazacyclononane", *Bulletin of the Academy of Sciences of the USSR; Division of Chemical Science*, 33, (1984),769-777.

Kaplan, E , et al., "Therapy of Carcinoma of the Prostate Metastic to Bone with P32 Labeled Condensed Phosphate", *The Journal of Nuclear Medicine*, 1, (1960),1-13.

Kasi, L. P., et al., "Ho-166DOTMP: A New Agent for Bone Marrow Ablation", *The Journal of Nuclear Medicine*, 34, Abstract Book, Proceedings of the 40th Annual Meeting, Toronto, Ontario, Canada, Abstract No. 125,(1993),33P.

Keeling, A. A., et al., "Yttrium-90-EDTMP: A Radiotherapeutic Agent in the Treatment of Leukaemias", *British Journal of Cancer*, 60, (1989),74-78.

Ketring, A R., "153Sm-EDTMP and 186Re-HEDP as Bone Therapeutic Radiopharmaceuticals", *Nucl. Med. Biol.*, 14(3), (1987),223-232.

Kohn, D B., "The Current Status of Gene Therapy Using Hematopoietic Stem Cells", *Currunt Opinion in Pediatr.*, 7, (1995),56-63.

Kothari, K K., et al., "186RE and 188RE Phosphonate Ligands", *The Journal of Nuclear Medicine*, 40, Proceedings of the 46th Annual Meeting, Abstract No. 1015,(1999)228P.

Krishnamurthy, G. T., et al., "Tin-117m(4+)DTPA: Pharmacokinetics and Imaging Characteristics in Patients with Metastatic Bone Pain", *The Journal of Nuclear Medicine*, 38, (1997),230-237.

Krivit, W , et al., "Bone Marrow Transplantation as Effective Treatment of Central Nervous System Disease in Globoid Cell Leukodystrophy, metachromatic leukodystrophy, adrenoleukodystrophy, mannosidosis, fucosidosis, aspartylglucosaminuria, Hurler, Maroteaux-Lamy, and . . . ", *Curr Opin Neurol*, 12(2), (1999),167-176.

Kyle, et al., "Multiple Myeloma", *The New England Journal of Medicine*, 351, (2004),1860-1873.

Larsen, et al., "Preliminary Evaluation of a New Radiolabelled Bisphosphonate", *Journal of Labelled Compounds and Radiopharmaceuticals, XLI*, (1998),823-830.

Logan, K W., et al., "Radiation Dose Calculations in Persons Receiving Injection of Samarium-153-EDTMP", *J. Nucl. Med.*, 28, (1987),505-509.

MA, J , et al., "Indium-113m Labeled Bone Imaging Agents-13 Animal Experiment and Clinical Application of 113mIn-DTPMP and 113mIn-EDTMP", *Chemical Abstracts*, 93, (1980),285.

Mathieu, L. , et al., "Preparation of Rhenium-186 Labelled EHDP and its Possible Use in the Treatment of Osseous Neoplasms", *International Journal of Applied Radiation and Isotopes*, 30, (1979),725-727.

McCullough, S P., et al., "99mTc-MDP as a Surrogate Quantitative Imaging Agent for High Dose 166Ho-DOTMP Bone Marrow Ablation Therapy", *Society of Nuclear Medicine Proceedings of the 47th Annual Meeting*, 41(5), (2000),147P.

McCullough, S. P., et al., "Non-target Organ Doses in Patients Undergoing Bone Marrow Ablation with Ho-166-DOTMP", *The Journal of Nuclear Medicine*, 39, No. 5, Abstract Book, Scientific Abstracts of the 45th Annual Meeting of the Society of Nuclear Medicine, Toronto, Ontario, Canada, Abstract No. 838,(1998),186P.

McCullough, S P., et al., "Pharmacokinetics and Patient Specific Dosimetry of High Dose 166Ho-DOTMP Therapy Used for Treatment of Breast Cancer Metastatic to Bone", *The Journal of Nuclear Medicine: Proceedings of the 46th Annual Meeting*, 40, (1999),40P.

McCullough, S P., et al., "Preliminary Correlation of Bone Marrow Dose Distributions and Disease Response in Multiple Myeloma Patients Treated with Target Sketetal Radiotherapy", *The Journal of Nuclear Medicine, Proceedings of the 47th Annual Meeting*, 41(5), Abstract No. 327,(2000),83P.

Moreau, P , et al., "Melphalan 220 mg/m2 Followed by Peripheral Blood Stem Cell Transplantation in 27 Patients with Advanced Multiple Myeloma", *Bone Marrow Transplant*, 23(10), (1999),1003-1006.

Nail, S L., "The Relationship Between the Structure of Aluminum Hydride Gel and Acid Reactivity", *Chemical Abstracts*, 84, (1976),353.

O'Mara, R E., et al., "Rare Earth Nuclides as Potential Agents for Skeletal Imaging", *The Journal of Nuclear Medicine*, 10, (1969),49-51.

Parks, N. J., et al., "Bone Marrow Transplantation in Dogs After Radio-Ablation with a New Ho-166 Amino Phosphonic Acid Bone-Seeking Agent (DOTMP)", *Blood*, 82 (1), (1993),318-325.

Paulson, Tom , "Seattle Leads in Stem Cell Study: Fred Hutchinson Team Explores Options with Autoimmune Project", *The Seattle Post-Intelligencer*, (1999).

Podoloff, D A., et al., "Phase I/II Studies of Holmium-166 DOTMP in Combination with Melphalan with or without Total Body Irradiation as a Preparative Regimen For Autologous Stem Cell Transplant (PBSCT) for Patients with Multiple Myeloma (MM)", *European Journal of Nuclear Medicine*, 26(9), Abstract No. PS-641,(1999),1213.

Podoloff, D. A., et al., "Phase I/II Study of Holmium-166-DOTMP for Bone Marrow Ablation in Multiple Myeloma Prior to Bone Marrow Transplantation (BMT)", *The Journal of Nuclear Medicine*, 35, Abstract Book, Proceedings of the 41st Annual Meeting, Orlando, FL, Abstract No. 139,(1994),37P.

Podoloff, Donald A., "The Role of Radioisotopes and the Treatment of Solid Tumors", *Accomplishments with Medical Isotopes: Advanced Health Care for the 21st Century*, Medical Isotopes and the 21st Century,(1999).

Podoloff, D. A., et al., "Update on the Ho-166 DOTMP Bone Marrow Ablation Trial at U.T.M.D. Anderson Cancer Center", *Journal of Nuclear Medicine*, 37, Supplement: Radiolabeled IUdr, Abstract No. 1053,(1996),234P.

Rajendran, J G., et al., "High Dose Holmium-166 DOTMP Myeloablative Treatment for Multiple Myeloma", *Journal of Nuclear Medicine*, Proceedings of the 47th Annual Meeting,(2000),146P.

Rajendran, et al., "High-Dose 166Ho-DOTMP in Myeloablative Treatment of Multiple Myeloma: Pharmacokinetics, Biodistribution, and Absorbed Dose Estimation", *J Nucl Med*, 43, (2002),1383-1390.

Rajendran, J G., et al., "Holmium-166 DOTMP: An Agent with Ideal Physical and Pharmacokinetic Characteristics for Use in Myeloablative Treatment of Multiple Myeloma", *Western Regional Soc. Nucl. Med.*, (2000).

Rosch, F. , et al., "Radiation Doses of Yttrium-90 Citrate and Yttrium-90 EDTMP as Determined via Analogous Yttrium-86 Complexes and Positron Emission Tomography", *European Journal of Nuclear Medicine*, 23, (1996),958-966.

Rosoff, B , et al., "Distribution and Excretion of Radioactive Rare-Earth Compounds in Mice", *International Journal of Applied Radiation and Isotopes*, 14, (1962),129-135.

Saltus, Richard , "Double Transplant's Success May Lead to End of Rejection Drugs", *The Seattle Post-Intelligencer*, (1999).

Schmidt, C G., et al., "89-Sr for the Treatment of Incurable Pain in Patient with Neoplastic Osseous Infiltrations", *Int. J. Clin. Pharmacol*, 9, (1974),199-205.

Sherry, A D., "31P and 23Na NMR Lanthanide Induced Shifts in Axially Symmetric Macrocyclic Phosphonate Complexes", *Inorganica Chimica Acta*, 139, (1987),137-139.

Sherry, A D., et al., "Dy(DOTP)5-: A New, Stable, 23Na Shift Reagent", *Journal of Magnetic Resonance*, 76, (1988),528-533.

Shibata, Y , et al., "Selectively Eliminated Blood Monocytes and Splenic Suppressor Macrophages in Mice Depleted of Bone Marrow by Strontium 89", *J. Leukocyte Biol.*, 38, (1985),659-669.

Simon, J , et al., "153Sm-EDTMP, a Potential Therapeutic Bone Agent", Sixth International Symposium on Radiopharmaceutical Chemistry: Abstracts. Boston, Jun. 29-Jul. 3, 1986. Paper 141,(1986),320-322.

Spiers, F W., et al., "Mean Skeletal Dose Factors for Beta-particle Emitters in Human Bone. Part II: Surface-seeking Radionuclides", *British Journal of Radiology*, 54, (1981),500-504.

Srivastava, S C., et al., "Ruthenium-97 Labeled Compounds—A New Class of Radiopharmaceuticals", *Front. Nucl. Med.*, (*Sel. Pap. Int. Congr. World Fed. Nucl. Med. Biol.*), 2nd, EDITOR: Horst, Wolfgang (Ed), Wagner, Henry N., Jr. (Ed), Buchanan, Julia W (Ed),(1980),123-133.

Stabin, M G., et al., "Bremsstrahlung Radiation Dose in Yttrium-90 Therapy Applications", *J Nucl Med*, 35, (1994),1377-1380.

Subramanian, G , et al., "Indium-113m Labeled Polyfunctional Phosphonates as Bone Imaging Agents", *Chemical Abstracts*, 87, (1977),243.

Subramanian, G , et al., "Indium-113m-Labeled Polyfunctional Phosphonates as Bone-Imaging Agents", *Journal of Nuclear Medicine*, 16, (1975),1080-1084.

Subramanian, G , et al., "Localization of new Tc-99m Labeled Diphosphonates in Experimental Bone Lesions", Presented at the 19th International Annual Meeting of the Society of Nuclear Medicine Europe, Bern, Switzerland, Sep. 8-11, 1981,(1981).

Swailem, Fayez , et al., "In vivo Tissue Uptake and Retention of Sn-117m(4+)DTPA in a Human Subject with Metastatic Bone Pain and in Normal Mice", *Nuclear Medicine & Biology*, 25, (1988),279-287.

Tananaev, I V., et al., "Lanthanide Ethylenediametetramethylphosphonates", *Chemical Abstracts*, 96, (1982),553.

Thomas, E D., "Clinical Trials with Bone Marrow Transplantation", *Clinical Trials in Cancer Medicine*, Academic Press, Inc. ,(1985),239-253.

Thomas, E D., "Marrow Transplantation for Malignant Diseases", *Journal of Clinical Oncology*, 1, (1983),517-531.

Thomas, E D., et al., "Marrow Transplantation for Thalassemia", *Annals New York Academy of Sciences*, 445, (1985),417-427.

Thomas, S R., "MIRD Pamphlet No. 14: A Dynamic Urinary Bladder Model for Radiation Dose Calculations.", *Journal of Nuclear Medicine*, 33, Published erratum appears in Journal of Nuclear Medicine, 35, 73 (1994).,(1992),783-802.

Turner, J H., et al., "Radiopharmaceutical Therapy of 5T33 Murine Myeloma by Sequential Treatment with Samarium-153 Ethylenediaminetetramethylene Phosphonate, Melphalan, and Bone Marrow Transplantation", *Journal of the National Cancer Institute*, 85(18), (1993),1508-1513.

Turner, J. H., et al., "Samarium—153 EDTMP Therapy of Disseminated Skeletal Metastasis", *Eur. J. Nucl Med*, 15, (1989),784-795.

Turner, J. H., et al., "Samarium-153 EDTMP and melphalan chemoradiotherapy regimen for bone marrow ablation prior to marrow transplantation in the C5t7BL/KalwRij mouse as a model for treatment of multiple myeloma", *Australian & New Zealand J of Medicine*, 22, (1992),405.

Turner, J. H., et al., "Samarium-153 EDTMP and melphalan chemoradiotherapy regimen for bonemarrow ablation prior to marrow transplantation: an experimental model in the rat", *Nuclear Medicine Communications*, 13(5), (1992),321-329.

Volkert, W A., et al., "Characteristics of Tc-99m-Complexes of Large Tetraphosphonates", 1984 Abstract Form for Scientific Exhibits Society of Nuclear Medicine 31st Annual Meeting, Los Angeles, California, June 5-8, 1984.

Weininger, J , "Re-186 HEDP: A Potential Therapeutic Bone Agent", *Journal of Nuclear Medicine*, 24(5), Proceedings of the 30th Annual Meeting—Posters,(1983),P125.

Wendt, R E., "An Improved Estimate of Activity in Skull-Like Structures", *Journal of Nuclear Medicine*, 42, Proceedings of the 48th Annual Meeting,(2001),193P.

Wendt, R E., et al., "Correction of Scatter and Septal Penetration in Ho-166 Images to Enable Narrow Beam Attenuation Correction", *Journal of Nuclear medicine*, 43(5),(2002),221P-222P.

Winston, M A., "Radioisotope Therapy in Bone and Joint Disease", *Seminars in Nuclear Medicine*, 9, (1979),114-120.

Wiseman, et al., "Bone Targeted Radioisotope Therapy for Treatment of Multiple Myeloma and Bone Tumors", *International Journal of Cancer Supplement*, 13, Abstract O 109; 18th UICC International Cancer Congress Oslo, Norway, Jun. 30-Jul. 5, 2002. ,(2002),104.

Wiseman, et al., "Residual Whole Body 153Samarium Activity Predicts for Successful Autologous Peripheral Blood Progenitor Cell (PBPC) Engraftment Following High Dose 153Samarium Ethylene Diamine Tetramethylene Phosphonate (153Sm-EDTMP) Targeted Radiotherapy", *Blood*, 96, Abstract 1811,(2000),421.

Young, J C., et al., "High Dose Samarium-153 Ethylenediaminetetramethylene Phosphate (SM-153 EDTMP) in the Treatment of Bone Sarcomas", *The Journal of Nuclear Medicine*, 40(5), Proceedings of the 46th Annual Meeting,(1999),219P.

Zeevaart, Jan R., et al., "Metal-ion Speciation in Blood Plasma Incorporating the Bisphosphonate, 1-hydroxy-4-aminopropilydenediphosphonate (APD), in Therapeutic Radiopharmaceuticals", *Journal of Inorganic Biochemistry*, 73, (1999),265-272.

\* cited by examiner

8

11

16

19

24

30

28

31

32

33

THERAPEUTIC AND DIAGNOSTIC COMPOUNDS, COMPOSITIONS, AND METHODS

RELATED APPLICATIONS

This application is a continuation of U.S. application Ser. No. 10/615,484, filed Jul. 8, 2003, now U.S. Pat. No. 7,115,720, issued Oct. 3, 2006, which is a continuation under 35 U.S.C. 111(a) of International Application Ser. No. PCT/US02/00629 filed 8 Jan. 2002 and published in English as WO 02/062398 on 15 Aug. 2002, which claims priority from U.S. Provisional Application Ser. No. 60/260,349 filed 8 Jan. 2001, which applications and publication are incorporated herein by reference.

BACKGROUND OF THE INVENTION

The invasive growth of cancer cells into bone tissues often results in severe pain syndromes and may ultimately result in death. Ionizing radiation has been used to achieve a reduction in pain. In particular, external radiation therapy has been applied in cases where bone pain is restricted to focal areas. For disseminated bone metastases, however, a treatment which focuses the radiation dose to bone tissue and particularly to bone metastases is desirable.

Prior to therapy it is necessary to obtain reliable diagnostic information and to this end several approaches have been tried. An approach that has been the subject of a number of patents, for example, U.S. Pat. No. 3,974,268 to Subramanian et al., involves the use of a technetium-99m diphosphonate complex as a skeletal imaging agent. This approach utilizes a diphosphonate as both the bone-seeking agent and the complexing agent for the radionuclide. Such an approach has at least three major disadvantages. First, by involving the bone-seeking agent in the complexation of the metal radionuclide, the ability of the agent to direct, or "target," the radionuclide to the desired site may be diminished. Second, because diphosphonate salts or chelates are known to form polymers, a preparation of diphosphonates and radionuclides typically includes multiple forms of diphosphonate-radionuclide complexes which have differing charge and uptake properties. Third, the complex formed between a diphosphonate and a radionuclide is not of optimal stability which may necessitate purification of the diphosphonate complex prior to use. Further, even a purified diphosphonate complex may lose the radionuclide during its use.

U.S. Pat. No. 4,853,209, is directed to the use of Sm-153, Gd-159, or Ho-166 complexed with a ligand selected from ethylenediaminetetramethylene-phosphonic acid (EDTMP), diethylenetriamine-pentamethylenephosphonic acid (DTPMP), hydroxyethylethylenediamine-trimethylenephosphonic acid (HEEDTMP), nitrilotrimethylenephosphonic acid (NTMP), and tris(2-aminoethyl)aminehexamethylenephosphonic acid (TTHMP), to suppress bone marrow growth.

U.S. Pat. No. 4,882,142, is directed to a method for the suppression of bone marrow and to a composition for use in the method. The method comprises administering a bone marrow suppressing amount of at least one composition comprised of a radionuclide Sm-153, Gd-159, or Ho-166, complexed with 1,4,7,10-tetraazacyclododecanemethylenephosphonic acid as the macrocyclic chelating moiety.

U.S. Pat. No. 5,059,412 is directed to compositions comprising a particle emitting radionuclide complexed with a macrocyclic aminophosphonic acid, wherein the nitrogen and phosphorous are interconnected by an alkylene group.

U.S. Pat. Nos. 5,202,109 and 5,089,249 are directed to conjugates formed from calcified tissue targeting agents and radiolabeled compounds. One conjugate comprises a chelate and a targeting agent that is capable of associating with calcified tissue, wherein the chelate contains at least one nitrogen atom or at least one sulfur atom, or a combination thereof.

In spite of the above disclosures, a continuing need exists for therapeutic and diagnostic agents that are useful for bone marrow suppression, cancer therapy, treating bone pain, and as diagnostic agents. Preferred agents may possess improved stability, improved uptake in bone, or improved retention in bone.

SUMMARY OF THE INVENTION

Applicant has discovered a group of structurally distinct radionuclide complexes that target bone, and thus, are useful as diagnostic (e.g., imaging) agents and as therapeutic agents (e.g., for bone marrow suppression, cancer therapy, treating bone pain, or treating other bone related diseases). Accordingly, the invention provides a complex of the invention comprising:

a) compound of formula I:

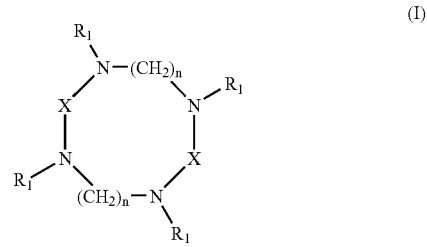

wherein:

each $R_1$ is independently hydrogen or $(C_1-C_4)$alkyl, optionally substituted with carboxy (COOH);

each X is independently $(CH_2)_n$ or

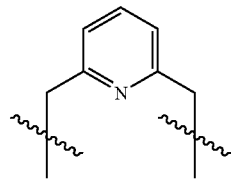

and each n is independently 2, 3, or 4;

wherein the compound of formula I is substituted on one or more (e.g. 1, 2, 3, or 4) carbons other than a carbon of $R_1$ with one or more (e.g., 1, 2, 3, or 4) groups $-Y(PO_3H_2)_m$; wherein Y is a linker group; and m is 1, 2, 3, 4, 5, or 6; or a pharmaceutically acceptable salt thereof;

b) a detectable or therapeutic radionuclide; and c) a radioprotectant.

The invention also provides a method for detecting the presence or absence of a calcified tissue target site within a mammal, comprising: administering to the mammal a detectable dose of a complex of the invention; and detecting the compound in the mammal to determine the presence or absence of the target site.

The invention also provides a therapeutic method for treating a bone related disease in a mammal in need of such therapy comprising administering to the mammal, an effective amount of a complex of the invention comprising a therapeutic radionuclide.

The invention also provides a therapeutic method for suppressing bone marrow in a mammal in need of such therapy comprising administering to the mammal, an effective bone marrow suppressing amount of a complex of the invention comprising a therapeutic radionuclide.

The invention also provides a therapeutic method for treating cancer in a mammal in need of such therapy comprising administering to the mammal, an effective amount of a complex of the invention comprising a therapeutic radionuclide.

The invention also provides a therapeutic method for treating bone pain in a mammal in need of such therapy comprising administering to the mammal, an effective amount of a complex of the invention comprising a therapeutic radionuclide.

The invention also provides a pharmaceutical composition comprising a complex of the invention and a pharmaceutically acceptable carrier.

The invention also provides a complex of the invention for use in medical therapy or diagnosis.

The invention also provides the use of a complex of the invention to prepare a medicament useful for suppressing bone marrow in a mammal, for treating cancer in a mammal, for treating bone pain in a mammal, or for treating a bone related disease in a mammal.

The invention also provides intermediates useful for preparing complexes of the invention (e.g., compounds of formula I), as well as processes useful for preparing complexes of the invention and for preparing compounds of formula I.

The present invention also provides compositions comprising a complex of the invention combined with an effective stabilizing amount of ascorbic acid or other stabilizing agent (e.g. gentisic acid) buffered to pH 7-8, as well as methods for preparing the compositions. The ascorbic acid maintains the radionuclide complex stability and reduces the amount of free radionuclide delivered in vivo. For example, ascorbic acid may be present in the unit dosage forms useful in the practice of the present invention at about 35-75 mg/ml of composition. Stabilization unexpectedly inhibits radiolytic degradation of the complexes, and thus allows distribution to hospitals at high levels of purity, with high levels of the radionuclide.

DETAILED DESCRIPTION

Figure 1:
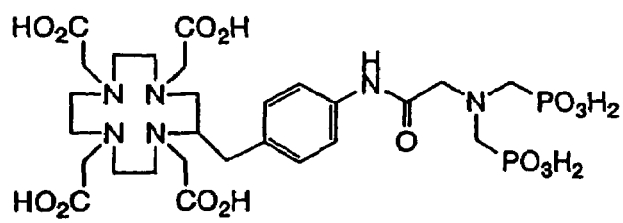
FIG. 1 illustrates representative compounds of formula (I)
Figure 1:
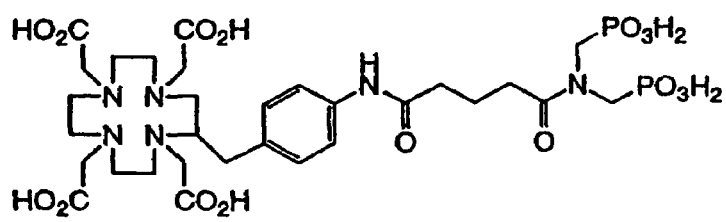
Figure 1:
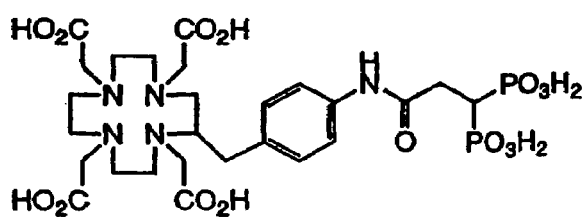
Figure 1:
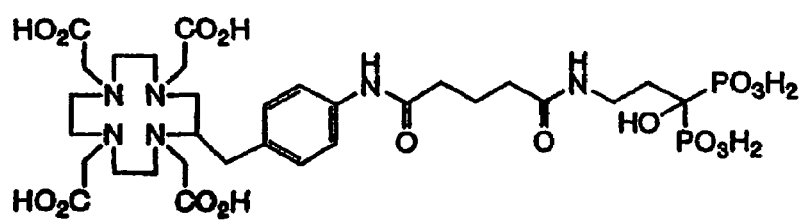
Figure 2:
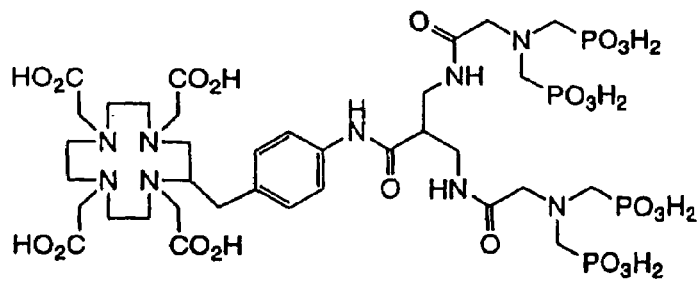
FIG. 2 illustrates representative compounds of formula (I)
Figure 2:
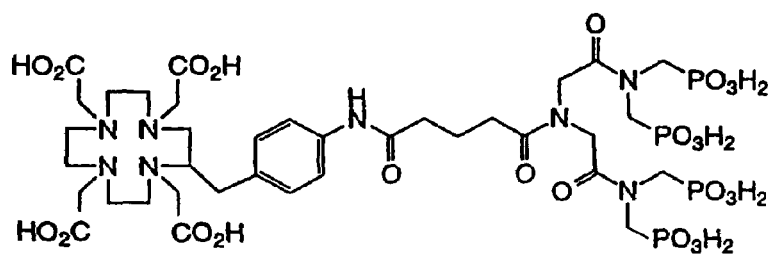
Figure 2:
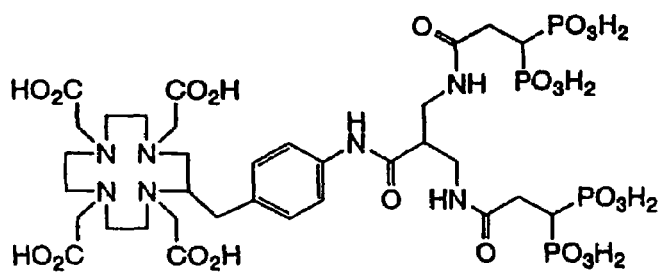
Figure 2:
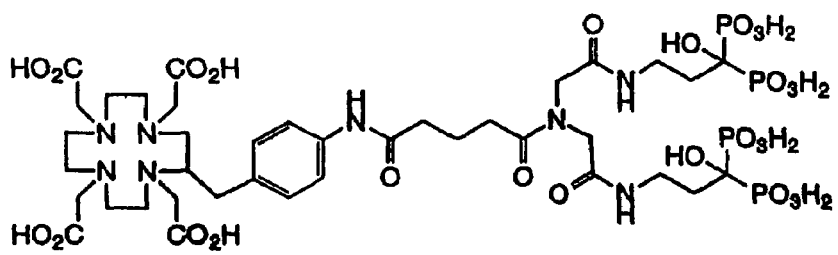
Figure 3:
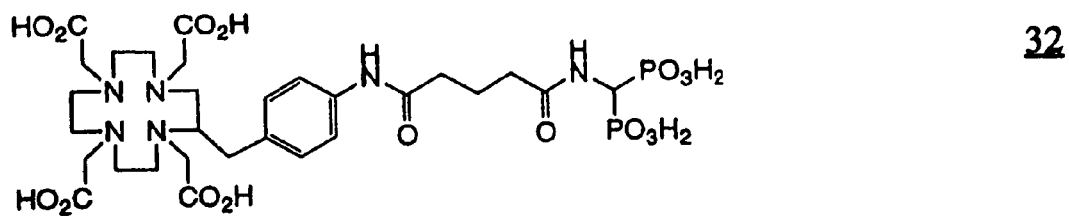
FIG. 3 illustrates representative compounds of formula (I)
Figure 3:
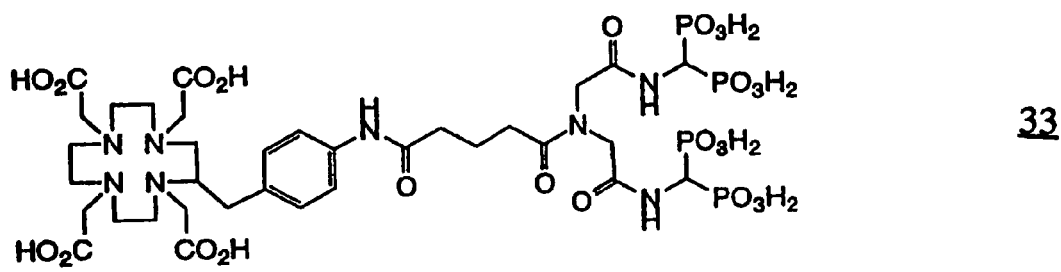

The following definitions are used, unless otherwise described: halo is fluoro, chloro, bromo, or iodo. Alkyl denotes both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

The term "bone marrow restoration" includes partial or complete regeneration or augmentation of the bone marrow by marrow transplantation or stem cell transplantation and/or stimulation of bone marrow regeneration by administration of growth factors such as cytokines, glycoproteins and the like.

The term "bone marrow transplant (BMT)" includes autologous, allogenic, xenogenic marrow transplantation and stem cell transplantation.

The term "calcified tissue" includes bone as well as other tissue that may be undergoing pathological calcification.

The term "disease" includes pathologies and deleterious conditions, such as inflammatory responses and genetic disorders.

The term "mammal" means a warm blooded mammal, including humans, and is meant to encompass mammals in need of bone marrow suppression, especially humans; thus in some instances the term "patient" or "subject" is alternatively used for mammal.

The term "suppressing bone marrow" includes partial or essentially total eradication (ablation or myeloablation) of the bone marrow, in particular, a temporary or permanent reduction of the hemopoietic stem cell population.

The present complexes and methods can also be employed to treat pathologies other than cancer associated with (at or near) mammalian bone, that can be ameliorated by partial bone marrow suppression or by complete bone marrow ablation followed by bone marrow transplantation. Thus, the term "bone related diseases" includes but is not limited to, immunological disorders such as autoimmune diseases, e.g., Crohn's disease, rheumatoid arthritis or multiple sclerosis; metabolic diseases, such as osteoporosis or osteopenia; infections and infectious disease, inflammatory diseases such as osteomyelitis or Paget's disease; hematopoietic disorders, and conditions treatable with stem cell transplantation, with or without gene therapy, that utilize bone marrow ablation, such as sickle cell anemia and lysosomal and peroxisomal storage diseases.

Complexes

Typically, the radionuclide complex is taken up preferentially by bone so that it is possible to deliver a bone marrow suppressing dose of radiation to the bone marrow. The radionuclide also should be cleared rapidly from the blood. The radiation exposure is reported using the Grey scale (Gy). The amount of radioactivity required to deliver a desired dose to marrow can be determined using a diagnostic dose of about 1200-2000 MBq (about 30 mCi to about 50 mCi) of the radionuclide/ligand. A determination of the doses of radiation delivered by the present complexes can be made using the methodologies of Bardies, M. and M. Myers (1996); "Computational methods in radionuclide dosimetry." *Physics in Medicine and Biology* 41: 1941-1955; Bayouth, J. (1993); A Dosimetric Study of Radionuclide Therapy for Bone Marrow Ablation. *Radiation Physics*, Houston, University of Texas—Houston Graduate School of Biomedical Science: 111; Beddoe, A. H., P. J. Darley, et al. (1976); "Measurements of trabecular bone structure in man." *Physics in Medicine & Biology* 21(4): 589-607; Bigler, R. and H. Woodard (1976); "Skeletal Distribution of Mineralized Bone Tissue in Humans." *Health Physics* 31(9): 213-218; Champlin, R. and R. Gale (1987); "Bone marrow transplantation for acute leukemia: recent advances and comparison with alternative therapies." *Semin. Hematol* 24: 55-67; Champlin, R. E. and R. P. Gale (1984); "Role of bone marrow transplantation in the treatment of hematologic malignancies and solid tumors: critical review of syngeneic, autologous, and allogeneic transplants." *Cancer Treatment Reports* 68(1): 145-61; Eckerman, K. and M. Stabin (1994); "Dose conversion factors for marrow and bone by skeletal regions; "*Journal of Nuclear Medicine(*35): 112P; Hiu, T. E. and J. W. Poston (1987). *A model of the circulating blood for use in radiation dose calculations*. Proceedings of International Conference on Radiation Dosimetry and Safety, Taipei, Taiwan, American Nuclear Society; I.C.R.P (1973). *Report of the task group on reference man: anatomical, physiological and metabolic characteristics*. New York, Pergamon Press; Loevinger, R. L., T. F. Budinger, et al. (1991); *MIRD Primer for Absorbed Dose Calculations*. New York, Society of Nuclear Medicine; Spiers, F. W., A. H. Beddoe, et al. (1981). "Mean skeletal dose factors for beta-particle emitters in human bone. Part II: surface-seeking radionuclides." *British Journal of Radiology* 54(642): 500-4; Thomas, S. R., M. G. Stabin, et al. (1992); "MIRD Pamphlet No. 14: a dynamic urinary bladder model for radiation dose calculations [published erratum appears in J. Nucl. Med. January1994;35(1):73*],*" *Journal of Nuclear Medicine* 33(5): 783-802.

It is important that the half-life of the complexed radionuclides be sufficiently long to allow for localization of the complex in the bone tissue, while still retaining sufficient radioactivity to accomplish bone marrow suppression or eradication. Generally, it is preferred to use a radionuclide complex that results in rapid biolocalization of the radionuclide in the bone tissue so as to achieve bone marrow irradiation quickly. It is also beneficial to use a radionuclide having sufficient beta energy, while having a relatively short half-life so that after bone marrow irradiation is achieved, it is possible to proceed with bone marrow or stem cell transplantation as soon as possible, in order to enhance the prospects of bone marrow engraftment and patient recovery.

Detectable or therapeutic radionuclides (i.e., radioisotopes or paramagnetic atoms) suitable for incorporation in the complexes of the invention include Antimony-124, Antimony-125, Arsenic-74, Arsenic-77, Barium-103, Barium-140, Beryllium-7, Bismuth-206, Bismuth-207, Bismuth-212, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-67, Erbium-169, Europium-152, Gallium-64, Gallium-68, Gadolinium-153, Gadolinium-157 Gadolinium-159, Gold-195, Gold-198, Gold-199, Hafnium-175, Hafnium-175-181, Holmium-166, Indium-110, Indium-111, Iridium-192, Iron-55, Iron-59, Krypton-85, Lead-203, Lead-210, Lutetium-177, Manganese-54, Mercury-197, Mercury-203, Molybdenum-99, Neodymium-147, Neptunium-237, Nickel-63, Niobium-95, Osmium-185+191, Osmium-193, Palladium-103, Platinum-195m, Praseodymium-143, Promethium-147, Promethium-149, Protactinium-233, Radium-226, Rhenium-186, Rhenium-188, Rubidium-86, Ruthenium-97, Ruthenium-103, Ruthenium-105, Ruthenium-106, Samarium-153, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-200, Thorium-228, Thorium-232, Thallium-170, Tin-113, Tin-114, Tin-117m, Titanium-44, Tungsten-185, Vanadium-48, Vanadium-49, Ytterbium-169, Ytterbium-175, Yttrium-86, Yttrium-88, Yttrium-90, Yttrium-91, Zinc-65, and Zirconium-95.

The term "detectable radionuclide" includes any suitable metallic radionuclide or paramagnetic atom that can be detected in a diagnostic procedure in vivo or in vitro.

The term "therapeutic radionuclide" includes any metallic radionuclide that is suitable to provide a therapeutic effect (e.g., bone marrow suppression or ablation, reducing bone pain, treating bone cancer, or treating a bone related disease), in a mammal. Such radionuclides should be capable of delivering a high enough localized ionization density to achieve a desired therapeutic result (e.g., alleviate pain, inhibit tumor growth, cause regression of a tumor, and/or destroy a tumor).

Radionuclides suitable for bone marrow suppression typically exhibit beta energy >0.5 MeV, preferably >1 MeV with an effective half-life of about <5 days, preferably <3 days. Certain radionuclides such as Strontium-89 have been demonstrated, when selectively deposited in bone, to suppress bone marrow. [See, for example, Y. Shibata et al., J. Leukocyte Biol. 38(6), 659-669 (December 1985).] However, this compound is not clinically useful for bone marrow replacement since the long half-life of Strontium-89 (50 days) prevents transplantation of the new marrow for an unacceptable time.

The term "amino acid," comprises the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g., acetyl or benzyloxycarbonyl), as well as natural and unnatural amino acids protected at the carboxy terminus (e.g., as a $(C_1-C_6)$alkyl, phenyl or benzyl ester or amide). Other suitable amino and carboxy protecting groups are known to those skilled in the art (See for example, T. W. Greene, *Protecting Groups In Organic Synthesis*, 2nd edition; Wiley: New York, 1991, and references cited therein). The term non-lipophilic amino acid comprises the natural amino acids Gly, Ser, Thr, Cys, Met, Asn, Gln, Tyr, Lys, Arg, His, Asp, and Glu in D and L forms, as well as unnatural amino acids of comparable degree of hydrophilicity—i.e., those lacking a hydrophobic side chain. An amino acid can be linked to the remainder of a compound of formula I through the carboxy terminus, the amino terminus, or through any other convenient point of attachment, such as, for example, through the sulfur of cysteine. The term amino acid also comprises natural and unnatural amino acids substituted on nitrogen with $(C_1-C_{10})$alkyl.

The term "saccharide" includes monosaccharides, disaccharides, trisaccharides and polysaccharides. The term includes glucose, sucrose fructose and ribose, as well as deoxy sugars such as deoxyribose and the like. Saccharide derivatives can conveniently be prepared as described in International Patent Applications Publication Numbers WO 96/34005 and 97/03995. A saccharide can conveniently be linked to the remainder of a compound of formula I through an ether bond.

The term "peptide" describes a sequence of 2 to 25 amino acids (e.g., as defined hereinabove) or peptidyl residues. The sequence may be linear or cyclic. For example, a cyclic peptide can be prepared or may result from the formation of disulfide bridges between two cysteine residues in a sequence. A peptide can be linked to the remainder of a compound of formula I through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right. Preferred peptides comprise primarily non-lipophilic amino acid residues (e.g., Gly, Ser, Thr, Cys, Met, Asn, Gln, Tyr, Lys, Arg, His, Asp, and Glu). Preferred peptides comprise one or more amino acids substituted on nitrogen with ($C_1$-$C_{10}$)alkyl.

For the diagnostic methods of the invention, the complexes of the invention can be detected using any imaging technique known in the art that is suitable for detecting the metal in the complex. Suitable imaging techniques for detecting complexes of the invention include PET, SPECT, and MRI.

The complexes of the invention are particularly useful for treating primary tumors, where the skeletal system is the first site of involvement, invasive tumors where the primary tumor invades the skeletal system or other tissue tumors which calcify, and metastatic bone cancer where a neoplasm spreads from other primary sites, e.g., prostate or breast, into the skeletal system.

The structure of the linker group Y is not critical, provided the complex of the invention comprising the linker group is suitable for its intended use as an imaging agent or as a therapeutic agent, and provided the linker group can be substituted with phosphono groups as provided for in the compounds of formula I. Therapeutic complexes comprising the linker group should be suitably stable and suitably non-toxic to allow for the complex to be administered to a mammal.

Specific and preferred values listed below for radicals, substituents, and ranges, are for illustration only; they do not exclude other defined values or other values within defined ranges for the radicals and substituents.

Specifically, ($C_1$-$C_{10}$)alkyl can be methyl, ethyl, propyl, isopropyl, butyl, iso-butyl, sec-butyl, pentyl, 3-pentyl, hexyl, heptyl, octyl, nonyl, or decyl; ($C_1$-$C_4$)alkyl can be methyl, ethyl, propyl, isopropyl, butyl, iso-butyl, or sec-butyl; and aryl can be phenyl, indenyl, or naphthyl.

A specific value for R' is ($C_1$-$C_4$)alkyl, substituted with carboxy.

Another specific value for $R_1$ is carboxymethyl or 2-carboxyethyl.

A specific value for n is 2 or 3.

Specifically, the linker group can separate the phosphono groups from the remainder of a compound of formula (I) by about 5 angstroms to about 100 angstroms. More specifically, the linker group can separate the phosphono groups from the remainder of a compound of formula (I) by about 10 angstroms to about 50 angstroms.

Specifically, the linker group can be an amino acid, a peptide, a saccharide, or a divalent ($C_1$-$C_{10}$)alkyl chain, optionally comprising one or more (e.g., 1, 2, 3, or 4) non-peroxide oxy (—O—), —N($R_d$)—, or divalent aryl within the chain or at the terminus of the chain, which chain is optionally substituted on carbon with one or more (e.g., 1, 2, 3, or 4) oxo (=O), thioxo (=S), or hydroxy, wherein $R_d$ is hydrogen or ($C_1$-$C_4$)alkyl.

Specifically, when the linker group is a peptide, it can comprise from 2 to about 25 amino acids residues.

Specifically, the linker group can be a divalent ($C_1$-$C_{10}$) alkyl chain, comprising one or more (e.g., 1, 2, 3, or 4) non-peroxide oxy (—O—), —N($R_d$)—, or divalent aryl within the chain or at the terminus of the chain, which chain is optionally substituted on carbon with one or more (e.g., 1, 2, 3, or 4) oxo (=O), thioxo (=S), or hydroxy, wherein $R_d$ is hydrogen or ($C_1$-$C_4$)alkyl.

Specifically, the linker group can be a divalent ($C_1$-$C_{10}$) alkyl chain, optionally comprising one or more (e.g., 1, 2, 3, or 4) non-peroxide oxy (—O—), —N($R_d$)—, or divalent aryl within the chain or at the terminus of the chain, which chain is substituted on carbon with one or more (e.g., 1, 2, 3, or 4) oxo (=O), thioxo (=S), or hydroxy, wherein $R_d$ is hydrogen or ($C_1$-$C_4$)alkyl.

Specifically, the linker group can be a divalent ($C_1$-$C_{10}$) alkyl chain comprising one or more (e.g., 1, 2, 3, or 4) non-peroxide oxy (—O—), —N($R_d$)—, or divalent aryl within the chain or at the terminus of the chain, which chain is substituted on carbon with one or more (e.g., 1, 2, 3, or 4) oxo (=O), thioxo (=S), or hydroxy, wherein $R_d$ is hydrogen or ($C_1$-$C_4$)alkyl.

Specifically, the group —Y($PO_3H_2$)$_m$ can be 4-[2-(Bis-phosphonomethyl-amino)-acetylamino]-benzyl; 4-[4-(Bis-phosphonomethyl-carbamoyl)-butyrylamino]-benzyl; 4-(3,3-Bis-phosphono-propionylamino)-benzyl; 4-[4-(3-hydroxy-3,3-bis-phosphono-propylcarbamoyl)-butyrylamino]-benzyl; 4-(3-[2-(Bis-phosphonomethyl-amino)-acetylamino]-2-{[2-(bis-phosphonomethyl-amino)-acetylamino]-methyl}-propionylamino)-benzyl; 4-(4-{Bis-[(bis-phosphonomethyl-carbamoyl)-methyl]-carbamoyl}-butyrylamino)-benzyl; 4-{3-(3,3-Bis-phosphono-propionylamino)-2-[(3,3-bis-phosphono-propionylamino)-methyl]-[propionylamino}-benzyl; 4-(4-{Bis-[(3-hydroxy-3,3-bis-phosphono-propylcarbamoyl)-methyl]-carbamoyl}-butyrylamino)-benzyl; 4-{4-[(Bis-phosphono-methyl)-carbamoyl]-butyrylamino}-benzyl; or 4-[4-(Bis-{[(bis-phosphono-methyl)-carbamoyl]-methyl}-carbamoyl)-butyrylamino]-benzyl.

A specific complex of the invention is a complex wherein the compound of formula (I) is a compound of formula II:

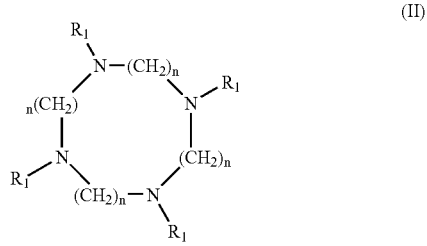

wherein:

each $R_1$ is independently hydrogen or $(C_1-C_4)$alkyl, optionally substituted with carboxy (COOH); and each n is independently 2, 3, or 4; wherein the compound of formula (II) is substituted on one or more (e.g. 1, 2, 3, or 4) carbons other than a carbon of $R_1$ with one or more (e.g., 1, 2, 3, or 4) groups —Y(PO$_3$H$_2$)$_m$; wherein Y is a linker group; and m is 1, 2, 3, 4, 5, or 6; or a pharmaceutically acceptable salt thereof.

Another specific complex of the invention is a complex wherein the compound of formula I is a compound of formula III:

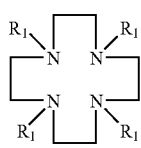

(III)

wherein each $R_1$ is independently hydrogen or $(C_1-C_4)$alkyl, optionally substituted with carboxy (COOH); and wherein the ring is substituted on carbon with one or more (e.g., 1, 2, 3, or 4) groups —Y(PO$_3$H$_2$)$_m$; wherein Y is a linker group; and m is 1, 2, 3,4, 5, or 6.

Another specific complex of the invention is a complex wherein the compound of formula (I) is a compound of formula (IV):

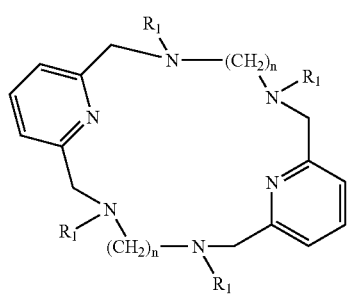

(IV)

wherein:

each $R_1$ is independently hydrogen or $(C_1-C_4)$alkyl, optionally substituted with carboxy (COOH); and each n is independently 2, 3, or 4; wherein the compound of formula IV is substituted on one or more (e.g. 1, 2, 3, or 4) carbons other than a carbon of $R_1$ with one or more (e.g., 1, 2, 3, or 4) groups —Y(PO$_3$H$_2$)$_m$; wherein Y is a linker group; and m is 1, 2, 3, 4, 5, or 6; or a pharmaceutically acceptable salt thereof.

Another specific complex of the invention is a complex comprising a compound of formula (I), (II), (III), or (IV) as described herein, wherein each $R_1$ is independently $(C_1-C_4)$ alkyl, substituted with carboxy (COOH); which compound is substituted with a group —Y(PO$_3$H$_2$)$_m$; wherein Y is a linker group; and m is 1, 2, 3, 4, 5, or 6.

A specific complex of the invention is a complex which comprises a detectable radionuclide.

A specific complex of the invention is a complex which comprises a therapeutic radionuclide.

A specific detectable radionuclide is Technetium-99m, Ruthenium-97, Indium-111, Gallium-67 or -68, or Lead-203.

A specific therapeutic radionuclide is Gadolinium-159, Holmium-166*, Lutetium-177, Samarium-153, Yttrium-90*, Ytterbium-175, Rhenium-186* or -188*, Copper-64 or -67, Gold-198 or -199, Bismuth-212, Scandium-46, -47, or -48, Gallium-72 or -73, Ruthenium-97, Palladium-100 or -109, Rhodium-101m or -105, Rhenium-189, Radium-212, or Lead-212

Specific radionuclides suitable for bone marrow suppression are Arsenic-77, Molybdenum-99, Ruthenium-105, Lutetium-177, Cadmium-115, Antimony-122, Promethium-149, Osmium-193, Gold-198, or Thorium-200. A more specific radionuclide suitable for bone marrow suppression is Samarium-153, Yttrium-90, Gadolinium-159, Rhenium-186 or -188, or Holmium-166. A preferred radionuclide for bone marrow suppression is Holmium-166, which emits high energy beta particles and imageable gamma radiation (80 KeV, 6%) and exhibits a half-life of 26.8 hr.

A specific therapeutic radionuclide is Holmium-166, Yttrium-90, Samarium-153, or Gadolinium-159.

A more specific therapeutic radionuclide is Holmium-166.

Processes and intermediates useful for preparing compounds of formula I and complexes of the invention are provided as further embodiments of the invention and are illustrated by the following procedures in which the meanings of the generic radicals are as given above unless otherwise qualified.

Radionuclide Complex Preparation

The radionuclide and the compound of formula I can be combined under any conditions that allow the two to form a complex. Generally, mixing in water at a controlled pH (the choice of pH is dependent upon the choice of ligand and radionuclide) is all that is required for formation of the complex. Following complexation, it may be necessary to adjust the pH to a level that is suitable for administration. The complex is typically formed by chelation of the radionuclide by an electron donor group or groups, which results in a relatively stable radionuclide complex, e.g., stable to the disassociation of the radionuclide from the ligand. Accordingly, the invention provides a method for preparing a complex of the invention comprising reacting a corresponding compound of formula I as described herein with a detectable or therapeutic radionuclide to provide the complex.

The invention also provides an intermediate compound of formula I:

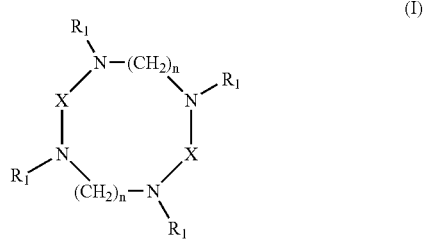

(I)

wherein:

each $R_1$ is independently hydrogen or $(C_1-C_4)$alkyl, optionally substituted with carboxy (COOH);

each X is independently $(CH_2)_n$ or

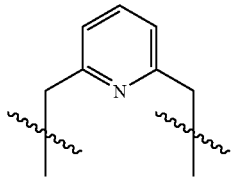

and each n is independently 2, 3, or 4;
wherein the compound of formula I is substituted on one or more (e.g. 1, 2, 3, or 4) carbons other than a carbon of $R_1$ with one or more (e.g., 1, 2, 3, or 4) groups —$Y(PO_3H_2)_m$; wherein Y is a linker group; and m is 1, 2, 3, 4, 5, or 6. Such an intermediate compound of formula (I) is useful for preparing a complex of the invention.

The invention also provides an intermediate compound of formula II, III, or IV as described herein.

A compound of formula I that comprises one or more carboxy groups (e.g., in $R_1$) can conveniently be prepared by deprotecting a corresponding compound wherein the carboxy groups are protected by a suitable carboxy protecting group (e.g., as a $(C_1$-$C_6$alkyl) or benzyl ester). Suitable protecting groups for carboxy groups as well as conditions suitable for their removal are well known in the art. For example, see Greene, T. W.; Wutz, P. G. M. "Protecting Groups In Organic Synthesis" second edition, 1991, New York, John Wiley & sons, Inc. Thus, the invention provides a method for preparing a compound of formula I wherein one or more of $R_1$ comprises a carboxy group comprising deprotecting a corresponding compound wherein one or more of the $R_1$ carboxy groups are protected by a suitable carboxy protecting group to provide the compound of formula I.

Accordingly, the invention also provides an intermediate compound of formula I:

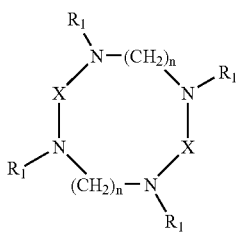

(I)

wherein:
each $R_1$ is independently $(C_1$-$C_4)$alkyl, substituted with COOR; R is a suitable carboxy protecting group (e.g., $(C_1$-$C_4)$alkyl or benzyl);
each X is independently $(CH_2)_n$ or

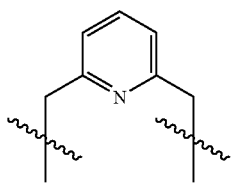

and each n is independently 2, 3, or 4;
wherein the compound of formula I is substituted on one or more (e.g. 1, 2, 3, or 4) carbons other than a carbon of RX with one or more (e.g., 1, 2, 3, or 4) groups —$Y(PO_3H_2)_m$; wherein Y is a linker group; and m is 1, 2, 3, 4, 5, or 6.

The invention also provides carboxy protected intermediate compounds of formula II, III, and IV as described herein wherein each $R_1$ is independently $(C_1$-$C_4)$alkyl, substituted with COOR; R is a suitable carboxy protecting group (e.g., $(C_1$-$C_4)$alkyl or benzyl).

A compound of formula I that is substituted with one or more (e.g., 1, 2, 3, or 4) groups —$Y(PO_3H_2)_m$ can conveniently be prepared by deprotecting a corresponding compound that is substituted with one or more (e.g., 1, 2, 3, or 4) groups —$Y(PO_3R_2)_m$ wherein R is a suitable phosphonic acid protecting group (e.g., a $(C_1$-$C_6$alkyl) or benzyl ester). Suitable protecting groups for phosphonic acid groups as well as conditions suitable for their removal are well known in the art. Thus, the invention provides a method for preparing a compound of formula I that is substituted with one or more (e.g., 1, 2, 3, or 4) groups —$Y(PO_3H_2)_m$ comprising deprotecting a corresponding compound that is substituted with one or more (e.g., 1, 2, 3, or 4) groups —$Y(PO_3R_2)_m$ wherein each R is a suitable phosphonic acid protecting group(s) (e.g., a $(C_1$-$C_6$alkyl) or benzyl ester), to provide the compound of formula I.

The invention also provides an intermediate compound of formula I:

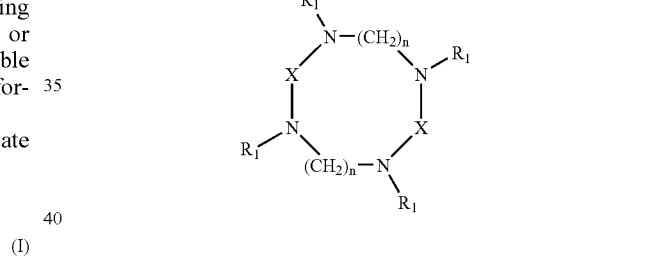

(I)

wherein:
each $R_1$ is independently $(C_1$-$C_4)$alkyl, substituted with COOR; R is a suitable carboxy protecting group (e.g., $(C_1$-$C_4)$alkyl or benzyl);
each X is independently $(CH_2)_n$ or

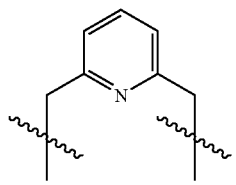

and each n is independently 2, 3, or 4;
wherein the compound of formula I is substituted on one or more (e.g. 1, 2, 3, or 4) carbons other than a carbon of R, with one or more (e.g., 1, 2, 3, or 4) groups —$Y(PO_3R_2)_m$; wherein Y is a linker group; each R is a suitable protecting group (e.g., $(C_1$-$C_4)$alkyl or benzyl); and m is 1, 2, 3, 4, 5, or 6.

The invention also provides phosphono protected intermediate compounds of formula II, III, and IV as described herein that are substituted on one or more (e.g. 1, 2, 3, or 4)

carbons other than a carbon of $R_1$ with one or more (e.g., 1, 2, 3, or 4) groups —$Y(PO_3R_2)_m$; wherein Y is a linker group; each R is a suitable protecting group (e.g., $(C_1-C_4)$alkyl or benzyl); and m is 1, 2, 3, 4, 5, or 6.

Radionuclide Preparation

The respective radionuclides can be obtained using procedures well known in the art. Typically, the desired radionuclide can be prepared by irradiating an appropriate target, such as a metal, metal oxide, or salt. Another method of obtaining radionuclides is by bombarding nuclides with particles in a linear accelerator or cyclotron. Yet another way of obtaining radionuclides is to isolate them from fission product mixtures. The method of obtaining the radionuclide is not critical.

Stabilizing Agents

A pharmaceutically acceptable means of protecting the complexes of the invention from radiolytic decay can be employed. Preferred radioprotectants of the present invention are anti-oxidants, compounds that either reduce the number or the activity of oxidizing radicals. Exemplary radioprotectants that can be employed in the practice of the present invention are ascorbic acid, gentisic acid, nicotinic acid, ascorbyl palmitate, $HOP(O)H_2$, monthioglycerol, sodium formaldehyde sulfoxylate, $Na_2S_2O_5$, $Na_2S_2O_3$, $SO_2$, or a reducing agent combined with BHA, BHT, pyrogallate or tocopherol and the like. Ascorbic acid is the preferred radioprotectant for use in the practice of the present invention, and can be used at about 35-75 mg/mL of liquid composition.

The formulations of the present invention can be in solid or liquid form, containing the active radionuclide complexed with the ligand. These formulations can be in kit form such that the chelator and radionuclide are mixed at the appropriate time prior to use in a suitable liquid carrier. Whether premixed or as a kit, the formulations usually require a pharmaceutically acceptable carrier.

Pharmaceutical Dosage Forms

The pharmaceutical dosage forms suitable for injection or infusion can include sterile solutions, dispersions, emulsions, or microemulsions, comprising the active ingredient which are adapted for the extemporaneous preparation of sterile injectable or infusible solutions or dispersions, optionally encapsulated in protective matrices such as nanoparticles or microparticles. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, phosphonate or carbonate esters, DMSO, and suitable mixtures thereof. The prevention of the action of microorganisms can be brought about by various antibacterial and antifungal agents, for example, benzyl alcohol, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Injectable suspensions as compositions of the present invention can comprise a liquid suspending medium, with or without adjuvants, as a carrier. The suspending medium can be, for example, aqueous polyvinylpyrrolidone, inert oils such as vegetable oils or highly refined mineral oils, or aqueous carboxymethylcellulose solutions. If necessary to keep the complex in suspension, suitable physiologically acceptable adjuvants can be chosen from among thickeners such as, for example, carboxymethylcellulose, polyvinylpyrrolidone, gelatin, and the alginates. Many surfactants are also useful as suspending agents, for example, lecithin, alkylphenol, polyethylene oxide adducts, naphthalenesulfonates, alkylbenzenesulfonates, and the polyoxyethylene sorbitan esters. Many substances which effect the hydrophobicity, density, and surface tension of the liquid suspension medium can assist in making injectable suspensions in individual cases. For example, silicone antifoams, sorbitol, and sugars are all useful suspending agents.

The "bone-marrow suppressing amount" or other effective therapeutic amount of radionuclide composition administered to achieve bone marrow suppression will vary according to factors such as the age, weight and health of the patient, the disease state being treated, the treatment regimen selected, as well as the nature of the particular radionuclide composition to be administered. For example, less activity will be needed for radionuclides with longer half lives. The energy of the emissions will also be a factor in determining the amount of activity necessary. The preferred range of activity per dose is from about 250 to about 3000 megabecquerels per kilogram of body weight of said mammal. A more preferred dosage delivers from about 750 to about 2500 megabecquerels per kilogram of body weight of said mammal. The most preferred dosage can deliver from about 1000 to about 2000 megabecquerels per kilogram of body weight of said mammal. The effective amount will typically be administered, generally by administration into the bloodstream, in a single or multi-dose infusion.

The radionuclide compositions employed in the method of the present invention are capable of delivering a significant portion, preferably greater than about 15%, of the radioactivity present in the composition to bone tissue while not deleteriously affecting non-target soft tissues. Therefore, for those disease states where the treatment regimen requires bone marrow suppression, the present invention is particularly advantageous since it provides a means of achieving selective reduction in the hemopoietic cell population without having to resort to total body irradiation (TBI), thus resulting in minimal damage to non-target tissues. Furthermore, because there is a reduction in the radiation dose delivered to non-target tissues (as compared to the use of total body irradiation alone), the present invention offers the opportunity to use the same or increased amounts of conventional chemotherapeutic regimens. In addition, if it is desirable to employ total body irradiation in conjunction with the bone marrow suppression method described herein, for example, in the treatment of leukemia, it can be possible to reduce the radiation dosage used for the total body irradiation and still obtain the same or higher level of reduction of leukemic cells.

As used herein, the term "single dosage" or "single dose" means that the total dosage of radionuclide complex is administered in one (1) or more doses (unit dosage forms) within a short period of time, e.g., less than about 24 hours. Preferably the doses will be administered within 12 hours, most preferably 8 hours. More preferably the doses will be administered within 4 hours. More preferably the doses will be administered within 2 hours. Most preferably the dose will be administered as a single infusion, or other unit dosage form.

Bone Marrow Transplantation and Restoration

The general techniques of bone marrow transplantation are well known in the art, see for example, F. R. Appelbaum et al., "The Role of Marrow Transplantation in the Treatment of Leukemia", (pp. 229-262), C. D. Bloomfield (ed.), Chronic and Acute Leukemias in Adults, 1985, Martinus Nijhoff Publishers, Boston; E. D. Thomas, "Clinical Trials with Bone Marrow Transplantation", (pp. 239-253), Clinical Trials in Cancer Medicine, 1985, Academic Press, Inc.; E. D. Thomas, "Marrow Transplantation for Malignant Diseases", (pp. 517-531), Journal of Clinical Oncology, Vol. 1, No. 9 (September) 1983; E. D. Thomas et al., "Marrow Transplantation for Thalassemia", (pp. 417-427), Annals New York Academy of Sciences, 445, 1985.

Under general or spinal anesthesia and using standard marrow aspiration needles, multiple aspirates are performed from the anterior and posterior iliac crests and, occasionally, the sternum of the donor. The marrow is placed in heparinized tissue culture media and then, using metal screens, filtered to remove bony spicules and fat globules and to create a monocellular suspension. At the time of desired administration of the bone marrow, the marrow is infused intravenously, following which the marrow stem cells migrate to the marrow space, proliferate, and eventually restore normal hematopoiesis and immune function. It is preferable to give as many bone marrow cells as possible to enhance the prospects of marrow engraftment. Following allogeneic transplant the patient usually receives some form of immunosuppression, such as by administration of methotrexate or cyclosporine, in an attempt to prevent or at least modify graft-versus-host disease.

A more preferred method for retrieving bone marrow stem cells involves harvesting these cells from the peripheral blood to increase the concentration of stem cells in the blood by techniques such as negative selection with antibodies specific for hematopoietic cell markers. Patients are pretreated with chemotherapy, or pretreated with a colony stimulating factor such as G-CSF, GM-CSF, or SC-CSF. These cytokines are also used after TBI and marrow or stem cell transplant to enhance engraftment.

The use of high dose chemotherapy followed by stem cell support has become one of the most attractive therapeutic approaches in multiple myeloma since, in relation to conventional chemotherapy, it increases the number of complete remissions (CR), duration of event free survival (EFS) and probably, overall survival (OS). In this setting of high dose chemotherapy, the use of a complex of the invention to suppress (ablate) the marrow in order to potentially eradicate the malignant clone more effectively, requires stem cell support. With total marrow ablation using a complex of the invention a stem cell rescue is required using autologous stem cells collected prior to therapy. The ability to give back the patients stem cells post ablative therapy helps to regenerate the lost hematopoiesis and thus protect the patient from potentially life-threatening complications.

Treatment of Cancer

A. Chemotherapeutic Agents

In the treatment of a patient having a cancer such as leukemia or multiple myeloma, the use of the radionuclide compositions described herein can reduce or eliminate the neoplastic cell population in the bone marrow. The phosphonate complexes of the invention also provide enhanced penetration of bone and uptake of the radionuclide by neoplastic bone lesions, which represent areas of active bone matrix turnover. However, it will usually be necessary to administer one or more chemotherapeutic agents, such as melphalan, dimethyl busulfan, cytoxan and/or cyclophosphamide, to destroy the undesirable cells in locations other than the bone marrow or in sanctuaries within the bone marrow, or to add to the effects of the radiation. The efficacy of cancer elimination can be enhanced by the use of protein synthesis inhibitors, in order to inhibit repair of damaged DNA in the cancer cells.

Chemotherapy can be given in standard doses in conjunction with the present method, or as higher than standard doses along with the present invention, depending on the tolerance of the patient. In other instances in conjunction with the bone marrow suppression method of the present invention, it is often desirable to employ total body irradiation, with or without chemotherapeutic agents, as a treatment to reduce the malignant or neoplastic cell population, such as by delivering radiation to the patient from dual opposing cobalt-60 sources. Those skilled in the art will know how to perform a Phase I study determining the limits of tolerance of either the chemotherapy, irradiation or the dose of the present complexes or both.

Chemotherapeutic agents that are useful in practicing the present invention include but are not limited to adriamycin, ifosfamide, thiotepa, melphalan, methotrexate, mitoxantrone, estramustine, bleomycin, velban, taxanes, thalidomide, etoposide, phosphate, taxol, vincristine, dexamethasone, doxorubicin, busulfan, cytoxan, cyclophosphamide, bischloroethyl nitrosourea, cytosine arabinoaside, 6-thioguanine and the like. Preferred chemotherapeutic agents that are useful in practicing the present invention are adriamycin, ifosfamide, thiotepa, melphalan, methotrexate, mitoxantrone, estramustine, bleomycin, velban, taxanes, thalidomide, vincristine, dexamethasone, doxorubicin, busulfan and analogs thereof. For example, melphalan analogs are disclosed in U.S. Pat. Nos. 3,032,584 and 3,032,585 (see Merck Index (11th ed.) at page 914).

The term "chemotherapeutic agent" also includes anti-cancer agents, such as toxins, that are targeted to cancer cells by antibodies against cancer cell antigens. Such immunoconjugates are described in published PCT applications WO/97/00476 and WO/95/10940.

The mammals (patients) can also be treated with agents such as bisphosphonates, to counteract the hypercalcemia associated with certain tumors, such as lung cancers, multiple myeloma, renal cell carcinoma, bronchogenic carcinoma, breast cancer, lymphoma, and cancers of the head and neck. Pamidronate and alendronate disodium are preferred agents for treatment of this condition. It will be appreciated that the agents should be selected and used so as not to compete with the therapeutic agent for bone marrow uptake.

The mammals (patients) can be hydrated and premedicated with antiemetics to decrease nausea and vomiting that may be associated with suppression of bone marrow when practicing the present invention. The preferred antiemetics are those that reduce the irritation of the chemoreceptor trigger zone. Common regimens that are useful in practicing the present invention include serotonin 5-HT$^3$ antagonists such as, for example, ondansteron, granisetron, and the like; dopamine antagonists such as, for example, prochlorperazine, promethazine, droperidol, metoclopramide, and the like; antihistamines and anticholinergics such as, for example, diphenylhydramine, scopolamine, dimethylhydrinate, meclizine, and the like; corticosteroids such as, for example, dexamethasone and the like; and sedatives such as, for example, diazepam, lorazepam, and the like.

A wide variety of leukemias and solid tumors can be treated with the present complexes including bone-forming tumors, cartilage-forming tumors, fibrous and fibro-osseous tumors, leukemias such as chronic lymphocytic leukemia and myeloid leukemia, and metastatic tumors to the skeleton. These skeletal system tumors include, but are not limited to, sarcomas such as Ewing's sarcoma, osteochondroma, chondroma, chondroblastoma, chondromyxoid fibroma and chondrosarcoma, non-ossifying fibroma, fibrous histiocytoma, fibrosarcoma, liposarcoma, sarcoma of the periosteum, osteosarcoma, osteoma, osteoblastoma and giant cell tumor of the bone. Other tumors which can be treated include chordoma, adamanthoma, hemangioendothelioma, hemangiopericytoma, myelomas, such as multiple myeloma, non-Hodgkin's lymphoma, Hodgkin's disease, breast cancer, prostate cancer, lung cancer, head and neck cancer, ovarian cancer, bladder cancer, liver cancer, pancreatic cancer, renal cell carcinoma, myelodysplastic syndrome, germ cell tumor, and neuroblastoma, particularly those cancers that have metastasized to the bone, attach to the bone, or that are associated with the skeletal system. Myeloproliferative disorders, including polycythemia vera, macroglobulinemia, megakaryocytic myelosis or malignant histiocytosis, can also be treated with the present complexes.

Thus, the invention provides a method for treating cancer comprising administering to a mammal in need of such therapy, a complex of the invention comprising a therapeutic radionuclide, in combination with a chemotherapeutic agent, a bisphosphonate, or an antiemetic. The invention also provides a pharmaceutical composition comprising a complex of the invention and a chemotherapeutic agent, a bisphosphonate, or an antiemetics; in combination with a pharmaceutically acceptable carrier.

B. Adjunct Radiation Therapy

By careful aiming and regulation of dose, high-energy radiation can be used to destroy cancer cells in combination with the present radionuclide therapy. Radiation therapy (also referred to as radiotherapy, x-ray therapy, cobalt treatment, or irradiation) is presently either part of the treatment or the only treatment for about half of all cancer patients. This form of treatment is effective only for those cancer cells within the area receiving the radiation (the field), which can encompass the entirety of the subject's body (total body irradiation or TBI) or can be localized, as in the exposure of a specific tumor site.

Radiation may be used before surgery to shrink a cancerous tumor, after surgery to stop growth of any remaining cancer cells, or alone or with anticancer drugs to destroy a malignant tumor. It is particularly effective when used to treat certain types of localized cancers such as malignant tumors of the lymph nodes or vocal cords.

Radiation usually is not per se curative if the cancer cells have spread throughout the body or outside the area of radiation. It can be used even if a cure is not probable because it can shrink tumors, which decreases the pressure and pain they cause, or it can stop their bleeding.

Generally, radiation produces less physical disfigurement than radical surgery does, but it may produce severe side effects. These side effects are related to the damage x-rays do to normal tissue such as blood or bone marrow. Side effects include irritated skin, swallowing difficulties, dry mouth, nausea, diarrhea, hair loss, and a loss of energy. How serious and extensive these side effects become depend on where and how much radiation is used.

Use of the present radionuclide complexes can reduce or eliminate the need for total or targeted external radiation therapy, or can enhance the total efficacy of a therapeutic regimen which normally employs TBI. Doses of TBI useful in the present method can deliver total irradiation of from about 750-1350 cGy, e.g., about 800-1000 to 1200 cGy. The total irradiation may be given in multiple fractions, i.e., 1-10 fractions; or in a single dose.

Thus, the invention provides a method for treating cancer comprising administering to a mammal in need of such therapy, a complex of the invention, in combination with radiation therapy.

Treatment of Autoimmune Diseases and Immunosuppression

The methods and complexes of the invention are also useful to treat immunological disorders such as autoimmune diseases by immune suppression due to temporary partial bone marrow suppression or by marrow purging in combination with marrow transplantation. However, those skilled in the art would recognize that the methods and compositions of the invention can also be used for general immunosuppression in combination with other immunosuppressive therapies. Currently, autoimmune diseases are treated by a variety of nonspecific immunosuppressive drugs and steroids. One group of anti-inflammatory agents used in the treatment of autoimmune diseases is corticosteroids. Corticosteroids are synthetic versions of the body's hormone cortisone, which is produced in small amounts by the adrenal gland. Synthetically produced corticosteroids reduce inflammation and suppress the immune system. The most commonly prescribed corticosteroids for use in treating autoimmune disorders are prednisone and dexamethasone.

Autoimmune disorders are sometimes treated with immunosuppressant drugs such as cytotoxic agents (e.g., methotrexate, azathioprine and cyclophosphamide). In addition, anti-malarials including chloroquine and hydroxychloroquine can be used to suppress inflammation and the immune system in the treatment of autoimmune disorders. Autoimmune diseases can also be treated with nonsteroidal anti-inflammatory medications, such as aspirin, ibuprofen, naproxen, indomethacin, sulindac, etodolac and tolmetin. Gold salts have been used to treat autoimmune arthritis for over a half a century, while recent advances in research have yielded new autoimmune arthritis therapies, such as COX-2 inhibitors. COX-2 inhibitors (or super-aspirin) work to inhibit inflammation and pain without producing significant side effects. In addition, another class of agents that target aberrant cytokine production, such as anti-TNF (tumor necrosis factor) drugs, can also be used for the treatment for several types of arthritis including rheumatoid arthritis, lupus, myositis, and scleroderma.

Furthermore, the methods and complexes of the invention could also be used alone or in combination with drugs that act more specifically on the immune system, for example, by blocking a particular hypersensitivity reaction. In addition, the complexes could be used in combination with intravenous immunoglobulin therapy or other antibody-based therapies, a treatment, used for various immunological diseases to reduce circulating immune complexes, or specific T cell populations. For example, the present methods and complexes can be used as immunosuppressive agents to inhibit host rejection of transplanted cells, tissue or organs.

In order to increase the chance of the patient's recovery, it can be beneficial to employ materials, such as granulocyte macrophage colony stimulating factor (GM-CSF), or granulocyte colony stimulating factor (G-CSF), and IL-11 for thrombopoiesis to stimulate or enhance the regeneration and restoration of the bone marrow. It can also be beneficial to employ stem cell growth factor, G-CSF and/or GM-CSF prior to therapy to trigger release of stern cells into the blood where they can be collected.

Thus, the invention provides a method for treating an immunological disorder comprising administering to a mammal in need of such therapy, a complex of the invention, in combination with another immunosuppressant therapy or immunosuppressant drug. The invention also provides a pharmaceutical composition comprising a complex of the invention and an immunosuppressant drug; in combination with a pharmaceutically acceptable carrier.

Infections and Infectious Diseases

The methods and complexes of the invention are also effective to treat bacterial infections, fungal infections, and infectious diseases that localize to or around bone such as tuberculosis, bacterial osteomyelitis, fungal osteomyelitis, and the like. Anti-fungal agents, and anti-bacterial agents often have poor penetration into the bone and sites enclosed by bone such as the bone marrow. In situations in which the patient is suffering from an infectious disease which has localized to the bone, the patient may be able to achieve a cure by the delivery of high doses of radiation to the bone.

Examples of agents useful in combination with targeted radiation in practicing the present invention include, but are not limited to antibiotic agents, e.g., antibacterial urinary tract agents; anti-infective agents, anti-parasitic agents and anti-fungal agents, including those disclosed in The Physician's Desk Reference, 50th Edition, 1996.

Useful antibiotic agents include systemic antibiotics, such as aminoglycosides, cephalosporins (e.g., first, second, and third generation), macrolides (e.g., erythromycins), monobactams, penicillins, quinolones, sulfonamides, and tetracyclines, including those disclosed in The Physician's Desk Reference, 50th Edition, 1996.

In addition, antibacterial agents include 2-isocephem and oxacephem derivatives disclosed in U.S. Pat. No. 5,919,925; pyridonecarboxylic acid derivatives disclosed in U.S. Pat. No. 5,910,498; water miscible esters of mono- and diglycerides disclosed in U.S. Pat. No. 5,908,862; benzamide derivatives disclosed in U.S. Pat. No. 5,891,890; 3-ammoniopropenyl cephalosporin compounds disclosed in U.S. Pat. No. 5,872,249; 6-O-substituted ketolides disclosed in U.S. Pat. No. 5,866,549; benzopyran phenol derivatives disclosed in U.S. Pat. No. 5,861,430; pyridine derivatives disclosed in U.S. Pat. No. 5,859,032; 2-aminothiazole derivatives disclosed in U.S. Pat. No. 5,856,347; penem ester derivatives disclosed in U.S. Pat. No. 5,830,889; lipodepsipeptides disclosed in U.S. Pat. No. 5,830,855; dibenzimidazole derivatives disclosed in U.S. Pat. No. 5,824,698; alkylenediamine derivatives disclosed in U.S. Pat. No. 5,814,634; organic solvent-soluble mucopolysaccharides disclosed in U.S. Pat. No. 5,783,570; arylhydrazone derivatives disclosed in U.S. Pat. No. 5,760,063; carbapenem compounds disclosed in U.S. Pat. No. 5,756,725; N-acylpiperazine derivatives disclosed in U.S. Pat. No. 5,756,505; peptides disclosed in U.S. Pat. No. 5,714,467; oxathiazines and their oxides disclosed in U.S. Pat. No. 5,712,275; 5-amidomethyl alpha beta-saturated and -unsaturated 3-aryl butyolactone compounds disclosed in U.S. Pat. No. 5,708,169; halogenated benzene derivatives disclosed in U.S. Pat. No. 5,919,438; sulfur-containing heterocyclic compounds disclosed in U.S. Pat. No. 5,888,526; and oral antibacterial agents disclosed in U.S. Pat. No. 5,707,610.

Anti-parasitic agents include agents capable of killing arthropods (e.g., lice and scabies); helminths (e.g., ascaris, enterobius, hookworm, stronglyoids, trematodes, and trichuris); and protozoa (e.g., amebas, malaria, toxoplasma, and trichomonas), including those disclosed in The Physician's Desk Reference, 50th Edition, 1996.

The methods and compositions of the invention are also effective to treat fungal infections that localize to or around bone such as fungal osteomyelitis and the like. The methods and compositions can also be used in conjunction with antifungal agents known to be useful in the treatment of fungal infections. Antifungal agents include dermatological fungicides, topical fungicides, systemic fungicides, and vaginal fungicides, including those disclosed in The Physician's Desk Reference, 50th Edition, 1996.

In addition, antifungal agents include terpenes, sesquiterpenes diterpenes, and triterpenes disclosed in U.S. Pat. No. 5,917,084; sulfur-containing heterocyclic compounds disclosed in U.S. Pat. No. 5,888,526; carbozamides disclosed in U.S. Pat. No. 5,888,941; phyllosilicates disclosed in U.S. Pat. No. 5,876,738; corynrcandin derivatives disclosed in U.S. Pat. No. 5,863,773; sordaridin derivatives disclosed in U.S. Pat. No. 5,854,280; cyclohexapeptides disclosed in U.S. Pat. No. 5,854,213; terpene compounds disclosed in U.S. Pat. No. 5,849,956; agents derived from aspergillus fumigatus disclosed in U.S. Pat. No. 5,873,726; inula extracts disclosed in U.S. Pat. No. 5,837,253; lipodepsipeptides disclosed in U.S. Pat. No. 5,830,855; polypeptides disclosed in U.S. Pat. No. 5,824,874; pyrimidone derivatives disclosed in U.S. Pat. No. 5,807,854; agents from sporomiella minimizes disclosed in U.S. Pat. No. 5,801,172; cyclic peptides disclosed in U.S. Pat. No. 5,786,325; polypeptides disclosed in U.S. Pat. No. 5,773,696; triazoles disclosed in U.S. Pat. No. 5,773,443; fusacandins disclosed in U.S. Pat. No. 5,773,421; terbenzimidazoles disclosed in U.S. Pat. No. 5,770,617; and agents obtained from hormones disclosed in U.S. Pat. No. 5,756,472.

Thus, the invention provides a method for treating an infection or an infectious disease comprising administering to a mammal in need of such therapy, a complex of the invention, in combination with an antibiotic agent, an anti-infective agent, an anti-parasitic agent, or an anti-fungal agent. The invention also provides a pharmaceutical composition comprising a complex of the invention and an antibiotic agent, an anti-infective agent, an anti-parasitic agent, or an anti-fungal agent; in combination with a pharmaceutically acceptable carrier.

Pathologies Treatable by BMT or Stem Cell Replacement

The present methods can be useful to ablate bone marrow in treatment regimens intended to correct a variety of disorders by replacing "defective" hematopoietic cells, with "normal" autologous or allogeneic bone marrow or stem cells. This can be used in the treatment of diseases of red cells and bleeding disorders. These include hematopoietic genetic diseases such as hemolytic anemias, i.e., sickle cell anemia or thalassemia. Other such disorders include various anemias, polycythemia, thrombocytopenia, and bleeding disorders related to defective platelet function or abnormalities in clotting factors.

Hematopoietic stem cell transplantation from normal donor has been reported to be effective to treat lysosomal and peroxisomal storage diseases, such as globoid cell leukodystrophy, metachromatic leukodystrophy, adrenoleukodystrophy, mannosidosis, flucosidosis, aspartylglucosaminuria; Harder, Maroteaux-Lamy and Sly Syndromes and Gaucher disease type III. W. Krivit et al., *Curr. Opin. Neurol.*, 12, 167 (1999).

Gene Therapy

The present method can also be employed as part of gene therapy that involves implantation of genetically engineered stem cells, to correct genetic defects, following bone marrow ablation. For example, a subject's own stem cells can be "normalized" by introduction of a vector comprising a gene that will effectively counteract the defective gene or replace the missing one. See, D. B. Kohn, *Curr. Opinion in Pediatr.*, 7, 56 (1995).

Bone marrow suppression, followed by administration of genetically engineered (transformed) stem cells, can be used, for example, in the treatment of cancer in a human by inserting exogenous genes into human primary cells, such as, for example, stem cells, which specifically "target" mature blood cells to a tumor. Preferably, the stem cells have been removed from a cancer patient and expanded in culture. Genes that enhance the anti-tumor effects of the mature cells can also be employed. The blood cells can be expanded in number before or after insertion of the genes. A method for transforming blood cells is described in U.S. Pat. No. 5,286,497. Thus, the procedure is performed in such a manner that upon injection into the patient, the transformed blood cells will produce an anti-cancer agent in the patient's body, preferably at the site of the tumor itself.

The gene carried by the transformed stem cells can be any gene which directly or indirectly enhances the therapeutic effects of the resultant mature blood cells. The gene carried by the stem cells can be any gene which allows the blood cells to exert a therapeutic effect that it would not ordinarily have, such as a gene encoding a clotting factor useful in the treatment of hemophilia. Examples of other suitable genes include those that encode cytokines such as TNF, interleukins (interleukins 1-12), interferons ($\alpha$, $\beta$, $\gamma$-interferons), T-cell receptor proteins and Fc receptors for antigen-binding domains of antibodies, such as immunoglobulins.

Additional examples of suitable genes include genes that modify blood cells to "target" to a site in the body to which the blood cells would not ordinarily "target," thereby making possible the use of the blood cell's therapeutic properties at that site. In this fashion, blood cells can be modified, for example, by introducing a Fab portion of a monoclonal antibody into the stem cells, thereby enabling the mature blood cells to recognize a chosen antigen. Other genes useful in cancer therapy can be used to encode chemotactic factors which cause an inflammatory response at a specific site, thereby having a therapeutic effect. Other examples of suitable genes include genes encoding soluble CD4 which is used in the treatment of AIDS and genes encoding preselected polypeptides or protein that can act to correct or ameliorate genetic disorders which result in insufficient or defective enzymes. Such genes include the $\alpha$-antitrypsin gene, which is useful in the treatment of emphysema caused by $\alpha$-antitrypsin deficiency, a tyrosine hydroxylase gene (Parkinson's disease), a glucocerebrosidase gene (Gaucher's disease), an "$\alpha$-galactosidase gene (Fabray's disease) an arylsulfatase A gene (metachromatic leukodystrophies) or genes encoding other polypeptides or proteins.

The gene therapy of the present invention is also useful in the treatment of a variety of diseases including but not limited to adenosine deaminase deficiency, sickle cell anemia, thalassemia, hemophilia, diabetes, "-antitrypsin deficiency, brain disorders such as Alzheimer's disease, and other illnesses such as growth disorders and heart diseases, for example, those caused by alterations in the way cholesterol is metabolized and defects of the immune system.

One of skill in the art would recognize that the conditions discussed herein above can have multiple causes and can overlap in naming and categorization.

Salts

In cases where complexes are sufficiently basic or acidic to form stable nontoxic acid or base salts, administration as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, $\alpha$-ketoglutarate, and $\alpha$-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The amount of the complex or salt required for use in diagnosis or treatment will vary not only with the particular complex selected but also with the route of administration, the nature of the condition being treated and the age and condition of the patient, and will be ultimately at the discretion of the attendant physician or clinician. Typical dose ranges for imaging are 3-45 mCi per 70 kg body weight, preferably 5-35 mCi per 70 kg, more preferably 10-30 mCi per 70 kg. See Fritzberg et al. (U.S. Pat. No. 5,089,249). Typical dose ranges for therapy are 10-450 mCi per 70 kg body weight, preferably 20-300 mCi per 70 kg, more preferably 40-200 mCi per 70 kg. See Fritzberg et al. (U.S. Pat. No. 5,089,249).

The ability of a compound of the invention to suppress bone marrow growth can be determined using pharmacological models which are well known to the art. Examples of useful assays are found in Cleynhens, B. et al. (*Technetium, Rhenium, and Other Metals in Chemistry and Nuclear Medicine* (1999) p. 605), Larsen, R. H. et al. (*Journal of Labelled Compounds and Radiopharmaceuticals* XLI, 823 (1998)), Fritzberg et al. (U.S. Pat. No. 5,089,249), and Simon et al. (U.S. Pat. No. 5,064,633).

The invention will now be illustrated by the following non-limiting Examples wherein unless otherwise noted: reagents were obtained from Aldrich Chemical Co. (Milwaukee, Wis.); anhydrous solvents were obtained from Acros Organics (Fisher Scientific, Pittsburg, Pa.); other solvents were reagent or HPLC grade and obtained from Fisher Scientific; air sensitive reactions were carried out under nitrogen or argon; proton NMR spectra were obtained on a Varian Gemini-200 spectrometer; chemical shifts are expressed in parts per million ($\delta$) using residual solvent protons as internal standard; mass spectra were obtained using a ThermoQuest/Finnigan LCQ Detector (San Jose, Calif.) with an atmospheric pressure ionization (API) source and an electrospray ionization (ESI) probe; flash chromatography was carried out using Merck Silica Gel 60 (230-400 mesh); TLC was performed on pre-coated glass plates (Baker, Si250F with 254 nm fluorescent indicator), and spots were detected using UV light, iodine, ninhydrin spray (0.2% in EtOH) or an aqueous solution containing phosphomolybdic acid, $Ce(SO_4)_2$ and $H_2SO_4$; reverse phase flash chromatography was carried out using Bakerbond octadecyl (C-18) 40 µm Prep LC packing; reversed phase TLC was performed on pre-coated glass plates (EM Science RP-18 $F_{254S}$); analytical HPLC was carried out using a Waters 600 multisolvent delivery system and a Waters 490 programmable multiwavelength detector with a 5 µm C-18 column from Beckman Ultrasphere (Fullerton, Calif.); and preparative HPLC was performed on a Waters 3000 system with a Model 481 spectrophotometer (254 nm) using C-18 reversed phase columns from Microsorb (Walnut Creek, Calif.).

Compounds 1, 17 and 20 (FIGS. 4, 7, and 9) were synthesized by known literature procedures. (Yau, E. K.; Theodore, L. J.; Gustavson, L. M. U.S. Pat. No. 5,847,121 (Dec. 8, 1998); Kieczykowski, G. R.; Jobson, R. B.; Melillo, D. G.; Reinhold, D. F.; Grenda, V. J.; Shinkai, I. J. *Org. Chem.* 1995, 60, 8310-8312; and Nanjappan, P.; Raju, N.; Ramalingam, K.; Nowotnik, D. P. *Tetrahedron* 1994, 50, 8617-8632.)

EXAMPLE 1

Figure 4:
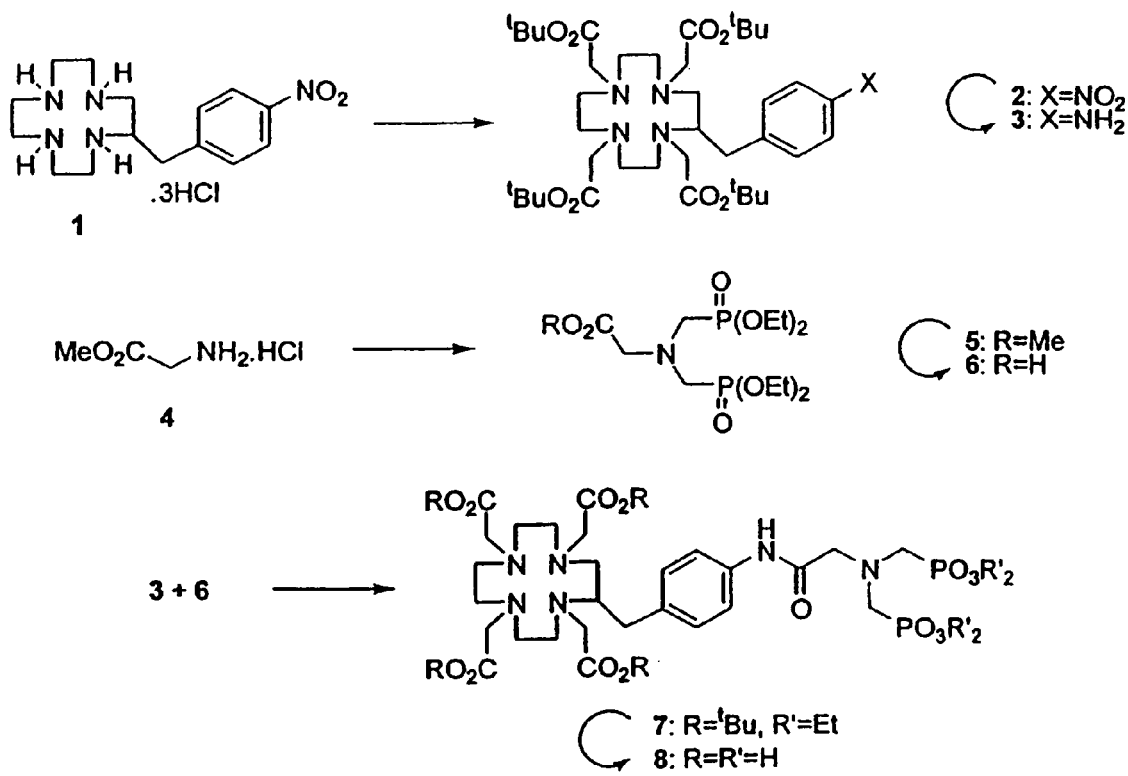
FIGS. 4-9 illustrate the synthesis of representative compounds of formula (I), and intermediates useful for preparing compounds of formula (I).

(6-{4-[2-(Bis-phosphonomethyl-amino)-acetylamino]-benzyl}-4,7,10-tris-carboxymethyl-1,4,7,10-tetraaza-cyclododec-1-yl)-acetic acid (8, FIG. 4)

To a solution of protected DOTA chelate 7 (49.2 mg; 45.1 µmol) in $CH_2Cl_2$ (3 mL) was added TMSBr (600 µL). The solution was stirred overnight, then $H_2O$ (1 mL) was added and stirring was continued for 30 minutes. Concentration yielded 66.1 mg of crude material which was purified by preparative HPLC on a C-18 reversed phase column using 100% $H_2O$ (containing 0.1% TFA) as the eluting solvent: Yield=15.6 mg (29%); $^1$H NMR ($D_2O$) δ 7.41 (d, 2H), 7.25 (d, 2H), 4.49 (s, 2H), 4.37-2.48 (complex multiplet, 25H), 3.68 (d, 4H); ESI-MS 755.2 (M+H), 777.2 (M+Na).

The intermediate protected DOTA chelate 7 was prepared as follows.

a. Tetra t-butyl nitrobenzyl DOTA 2 (FIG. 4). To a rapidly stirred solution of (S)-2-(p-Nitrobenzyl)-1,4,7,10-tetraaza-cyclododecane trihydrochloride salt 1 (350 mg; 0.84 mmol) and $K_2CO_3$ (1.16 g; 8.4 mmol) in anhydrous DMF (7 mL) was added t-butyl bromoacetate (0.62 mL; 4.2 mmol). The mixture was then heated to 50-55° C. and the progress of the reaction was monitored by HPLC. After 3 hours the mixture was cooled to room temperature then stored at 4° C. overnight. The precipitated solid was collected and rinsed with additional DMF (5 mL). This yielded 786 mg of crude material which was purified by silica gel chromatography, eluting with 0-10% $MeOH/CH_2Cl_2$, to yield 528 mg (82%) of 2. $R_f$=0.30 (10% $MeOH/CH_2Cl_2$); $^1$H NMR ($CDCl_3$) δ 8.17 (dd, 2H), 7.60 (d, 1H), 7.40 (d, 1H), 3.78-1.62 (complex multiplet, 25H), 1.49-1.37 (4s, 36H); ESI-MS 786.4 [M+Na].

b. Tetra t-butyl aminobenzyl DOTA 3 (FIG. 4). To a solution of nitrobenzyl compound 2 (528.7 mg; 0.69 mmol) in MeOH (50 mL) in a Parr shaker bottle was added 10% Pd/C (100 mg). The solution was then placed on the Parr apparatus under a hydrogen atmosphere of 50 psi. After 3 hours the solution was filtered and concentrated to yield 472 mg of crude material. Purification by silica gel chromatography, eluting with 0-10% $MeOH/CH_2Cl_2$ yielded 370 mg (73%) of 3. $R_f$=0.27 (10% $MeOH/CH_2Cl_2$); $^1$H NMR ($CDCl_3$) δ 6.75 (dd, 2H), 6.58 (dd, 2H), 3.43-1.45 (complex multiplet, 25H), 1.38-1.29 (4s, 36H).

c. Protected DOTA chelate 7 (FIG. 4). To a solution of aminobenzyl DOTA 3 (80.7 mg; 110 µmol) and amino acid hydrochloride 6 (50 mg; 121 µmol) in DMF (3 mL) was added benzotriazol-yl-oxy-tris(dimethylamino)phosphonium hexafluorophosphate (BOP; Chem-Impex International; Wood Dale, Ill.; 53.5 mg; 121 µmol) and DIEA (154 µL; 883 µmol). The mixture was stirred under argon at room temperature overnight then concentrated. The crude residue was dissolved in $CH_2Cl_2$ (20 mL) then washed with $H_2O$ (2×10 mL) and brine (10 mL) then dried ($MgSO_4$). Concentration gave 141 mg of crude material which was purified by silica gel chromatography, eluting with 0-8% $MeOH/CH_2Cl_2$, to yield 98.4 mg (82%) of protected DOTA chelate 7: $R_f$=0.45 (10% $MeOH/CH_2Cl_2$); $^1$H NMR ($CDCl_3$) δ 7.60 (dd, 2H), 7.07 (dd, 2H), 4.15 (pentet, 8H), 3.60 (s, 2H), 3.21 (d, 4H), 3.50-1.70 (complex multiplet, 25H), 1.49 (s, 9H), 1.47 (s, 9H), 1.44 (s, 9H), 1.41 (s, 9H), 1.33 (t, 12H).

The intermediate amino acid hydrochloride 6 was prepared as follows.

d. Methyl ester 5 (FIG. 4). (see U.S. Pat. Nos. 5,714,604, and 4,976,950). To a solution of paraformaldehyde (1.32 g; 44 mmol) and glycine methyl ester hydrochloride 4 (2.51 g; 20 mmol) in anhydrous THF (30 mL) was added triethylphosphite (7.54 mL; 44 mmol). The mixture was heated to reflux for 16 hours then cooled to room temperature and concentrated in vacuo. The material was dissolved in $CH_2Cl_2$ (100 mL) and washed sequentially with saturated aqueous $NaHCO_3$ solution (2×50 mL), $H_2O$ (50 mL) and saturated aqueous NaCl solution (50 mL). Drying ($MgSO_4$) and concentration yielded 7.208 g (93%) of methyl ester 4 which was of sufficient purity to be used in subsequent steps: $^1$H NMR ($CDCl_3$) δ 4.12 (m, 8H), 3.82 and 3.73 (2s, 2H), 3.69 and 3.65 (2s, 3H), 3.25 (t, 4H), 1.31 (t, 12H); ESI-MS 389.9 [M+H] and 412.1 [M+Na].

e. Amino acid hydrochloride 6 (FIG. 4). To a solution of methyl ester 5 (7.208 g; 18.5 mmol) in MeOH (30 mL) was added $H_2O$ (15 mL) followed by the dropwise addition of 1N—NaOH (22 mL). The mixture was stirred at rt overnight then concentrated. The crude material was dissolved in $H_2O$ (200 mL) and the aqueous solution washed with $CH_2Cl_2$ (2×100 mL) then acidified to pH-2 by the addition of 1N—HCl (22 mL). The aqueous solution was saturated with NaCl then extracted with 3:1 $CH_2Cl_2$:$^i$PrOH (3×150 mL). Drying ($MgSO_4$) and concentration in vacuo yielded 3.519 g (46%) of acid 6 which was of sufficient purity to be used in subsequent steps: $^1$H NMR ($CDCl_3$) δ 4.10 (pentet, 8H), 3.70 (s, 2H), 3.28 (d, 4H), 1.27 (t, 12H).

EXAMPLE 2

Figure 5:
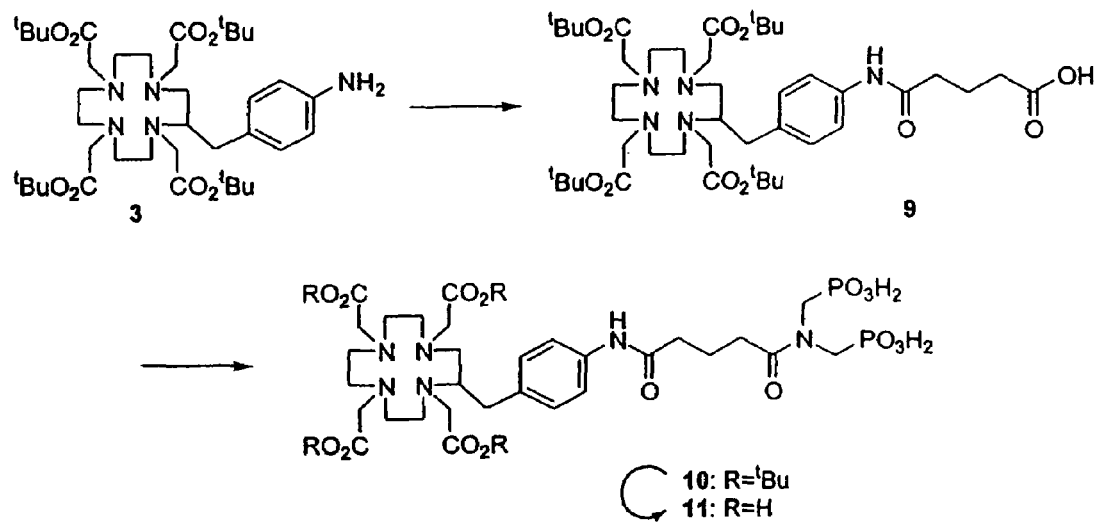

(6-{4-[4-(Bis-phosphonomethyl-carbamoyl)-butyrylamino]-benzyl}-4,7,10-tris-carboxymethyl-1,4,7,10-tetraaza-cyclododec-1-yl)-acetic acid (11, FIG. 5)

A solution of tetra t-butyl ester 10 (23.2 mg; 16.9 µmol) in TFA (5 mL) was stirred at room temperature overnight. Concentration followed by dissolution in $H_2O$ (12 mL) and lyophilization yielded 16.5 mg (85%) of 11 as a feathery white solid which was shown by HPLC to be of >98% purity: $^1$H NMR ($D_2O$) δ 7.34 (d, 2H); 7.21 (dd, 2H), 4.43-2.69 (complex multiplet, 27H), 2.58 (t, 2H), 2.40 (t, 2H), 1.92 (m, 2H); ESI-MS 811.2 (M+H), 833.2 (M+Na).

The intermediate tetra t-butyl ester 10 was prepared as follows.

a. DOTA linker acid 9 (FIG. 5). To a solution of DOTA aniline 3 (110.6 mg; 151 µmol) and glutaric anhydride (34.3 mg; 301 µmol) in anhydrous DMF (8 mL) was added DIEA (0.26 mL; 1.51 mmol). The solution was stirred overnight then concentrated in vacuo to yield 146 mg of crude material. Purification by preparative HPLC on a C-18 reversed phase column, eluting with $H_2O$/MeCN containing 0.1% TFA (using a gradient of 40-64% MeCN over 30 min) yielded 121 mg (67%) of 9 as its tri TFA salt: $^1$H NMR ($CD_3OD$) δ 7.55 (m, 2H), 7.30 (m, 2H), 4.53-2.52 (complex multiplet, 25H), 2.42 (2t, 4H), 1.97 (pentet, 2H), 1.70-1.40 (4s, 36H); ESI-MS 848.4 (M+H), 870.4 (M+Na).

b. Protected DOTA chelate 10 (FIG. 5). To a solution of acid 9 (45.2 mg; 38 µmol) in DMF (3 mL) was added BOP (18.5 mg; 41.8 µmol) followed by diisopropylethylamine (99 µL; 570 µmol). The solution was stirred, under argon, at room temperature for 30 min then iminobis(methylphosphonic acid) (8.6 mg; 41.8 µmol) was added. Progress of the reaction was monitored by HPLC. After 7 hours the solution was concentrated to give 107.4 mg of crude material, which was purified by preparative HPLC on a C-18 reversed phase column eluting with $H_2O$/MeCN containing 0.1% TFA (using a gradient of 40-64% $H_2O$ over 30 min). This yielded 23.2 mg (44%) of 10 as its tri TFA salt: ESI-MS 518.3 ([M+2H]/2), 1035.3 (M+H), 1057.3 (M+Na).

EXAMPLE 3

Figure 6:
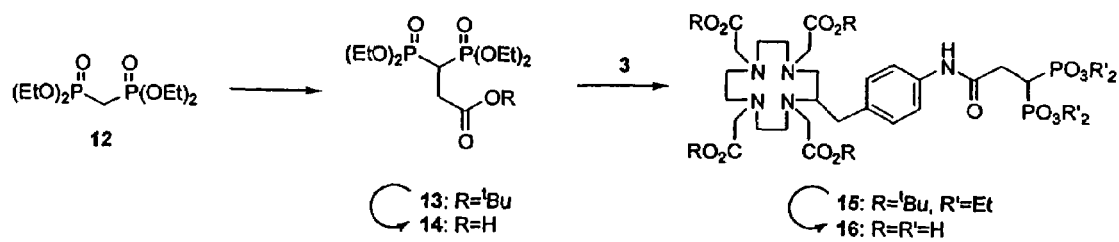

{3-[4-(3,3-Bis-phosphono-propionylamino)-benzyl]-4,7,10-tris-carboxymethyl-1,4,7,10-tetraaza-cyclododec-1-yl}-acetic acid (16, FIG. 6)

To a solution of compound 15 (132 mg; 124 µmol, FIG. 6) in $CH_2Cl_2$ (4 mL) was added trimethylsilyl bromide (1.25 mL). The mixture was stirred, under nitrogen, overnight. Water (1 mL) was added and stirring continued for 30 minutes. Concentration yielded 229 mg of crude material which was purified by preparative HPLC on a C-18 reversed phase column eluting with $H_2O$/MeCN containing 0.1% TFA (using a gradient of 0%-8% MeCN over 30 min). This yielded 49.7 mg (38%) of 16 as its tri trifluoroacetic acid salt: $^1$H NMR ($D_2O$) δ 7.31 (d, 2H), 7.16 (d, 2H), 4.39-2.40 (complex multiplet, 28H); ESI-MS 726.2 (M+H).

The intermediate compound 15 was prepared as follows.

a. t-Butyl ester 13 (FIG. 6. see Ebetino, F. H., et al., *Heterocycles* 1990. 30.855-862). To a slurry of KH (160 mg; 4.0 mmol) in mineral oil, under argon, was added anhydrous toluene (4 mL). The mixture was stirred for approximately 30 seconds then the solvents removed via syringe. This process was repeated. Additional toluene (4 mL) was added and the solution cooled on ice. A solution of tetraethyl methylenediphosphonate (0.75 mL; 3.0 mmol) in anhydrous toluene (8 mL) was added dropwise over 5 minutes. The ice bath was removed and the solution allowed to warm to rt. After 2 hours t-butyl bromoacetate (0.44 mL; 3.0 mL) was added dropwise. The solution was then heated to 80-85° C. for 2 hours then cooled to room temperature and quenched via the dropwise addition of MeOH (1 mL). Concentration followed by dissolution in $CH_2Cl_2$ (20 mL) and filtration (to remove insoluble KBr) then further concentration yielded 1.109 g (92%) of t-butyl ester 13. This material was of sufficient purity to be used in subsequent experiments: $^1$HNMR ($CDCl_3$) δ 4.18 (pentet, 8H), 3.21 (br s, 1H), 2.75 (dd, 2H), 1.45 (s, 9H), 1.31 (t, 12H); ESI-MS 425.0 (M+Na), 440.9 (M+K).

b. Acid 14 (FIG. 6). A solution of t-butyl ester 13 (555 mg; 1.4 mmol) in TFA (10 mL) was stirred at room temperature under nitrogen for 6 hours then concentrated. A quantitative yield was assumed and the material used immediately in the subsequent step: $^1$H NMR ($CDCl_3$) δ 4.19 (pentet, 8H), 3.15 (m 1H), 2.88 (dt, 2H), 1.37 (t, 12H).

c. Protected DOTA chelate 15 (FIG. 6). To a solution of acid 14 (83.1 mg; 240 µmol) and amine 3 (147 mg; 200 µmol) in DMF (3 mL) was added BOP (106 mg; 240 µmol) followed by diisopropylethyl amine (350 µL; 2.0 mmol). The solution was stirred, under nitrogen, at rt overnight then concentrated. The crude material was purified by flash chromatography ($SiO_2$; 0-7.5% MeOH/$CH_2Cl_2$) to give 132 mg (62%) of 15: $R_f$=0.46 (10% MeOH/$CH_2Cl_2$); $^1$H NMR ($CDCl_3$) δ 7.53 (dd, 2H), 7.03 (dd, 2H), 4.15 (m, 8H), 3.50-1.70 (complex multiplet, 28H) 1.45-1.35 (4s, 36H), 1.32 (m, 12H); ESI-MS 1084.4 (M+Na).

EXAMPLE 4

Figure 7:
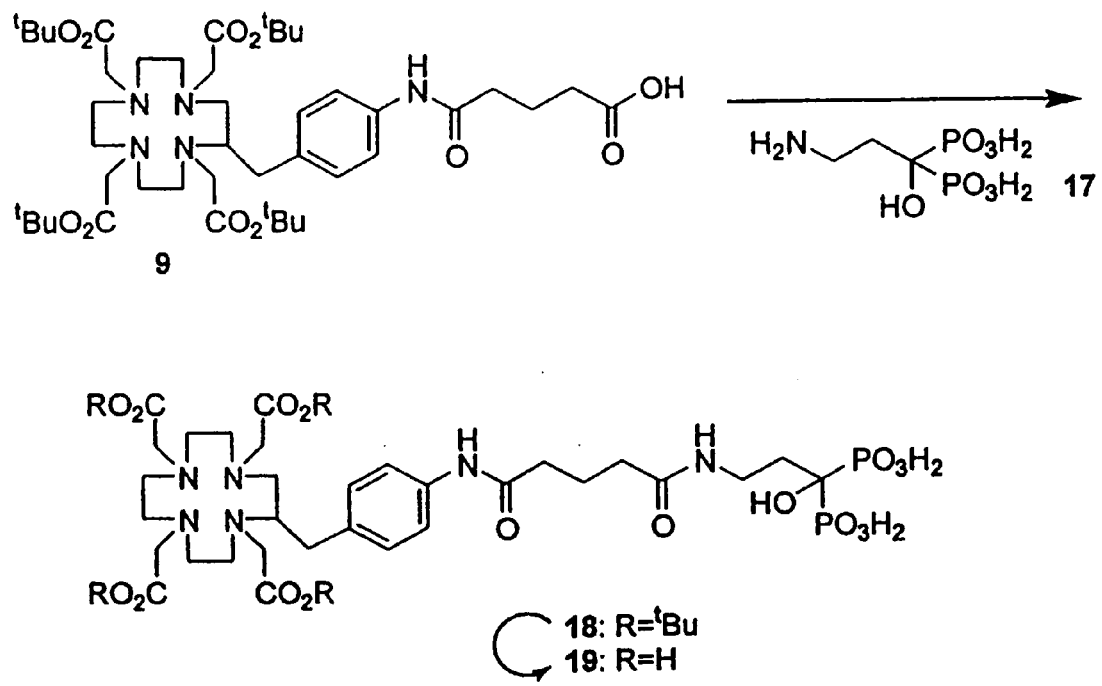

(4,7,10-Tris-carboxymethyl-3-{4-[4-(3-hydroxy-3,3-bis-phosphono-propylcarbamoyl)-butyrylamino]-benzyl}-1,4,7,10-tetraaza-cyclododec-1-yl)-acetic acid (19, FIG. 7)

A solution of compound 18 (32.4 mg; 22.7 µmol) in TFA (5 mL) was stirred under nitrogen at room temperature overnight. Concentration yielded 36.4 mg of crude material. Purification by preparative HPLC on a C-18 reversed phase column eluting with $H_2O$/MeCN containing 0.1% TFA (using a gradient of 0-16% MeCN over 30 min) yielded 18.6 mg (69%) of 19 as its tri TFA salt: $^1$H NMR ($D_2O$) δ 7.43 (m, 2H), 7.28 (m, 2H), 4.27-2.35 (complex multiplet, 36H); ESI-MS 533.8 ([M+H+Na]/2), 1042.3 (M+H), 1066.2 (M+Na).

The intermediate compound 18 was prepared as follows.

a. Compound 18 (FIG. 7). To a solution of acid 9 (59.9 mg; 50.3 µmol) in DMF (3 mL) was added BOP (26.7 mg; 60.4 µmol) followed by DIEA (87.7 µL; 503 µmol). The mixture was stirred for 10 minutes then a solution of the amino diphosphonate 17 (64.7 mg; 251.6 µmol) in $H_2O$ (2 mL) was added followed by additional DIEA (35 µL). Progress of the reaction was monitored by HPLC. After 16 hours the solution was filtered and the filter cake rinsed with DMF (5 mL). Concentration of the mother liquor yielded 143 mg of crude material which was purified by preparative HPLC on a C-18 reversed phase column eluting with $H_2O$/MeCN containing 0.1% TFA (using a gradient of 40-64% MeCN over 30 min) to provide 32.4 mg (45%) of compound 18 as its tri TFA salt: $^1$H NMR ($CD_3OD$) δ 7.56 (br s, 2H), 7.30 (br s, 2H), 4.55-1.73 (complex multiplet, 35H), 1.65-1.38 (4s, 36H); ESI-MS 1065.3 (M+H), 1087.3 (M+Na).

EXAMPLE 5

Figure 8:
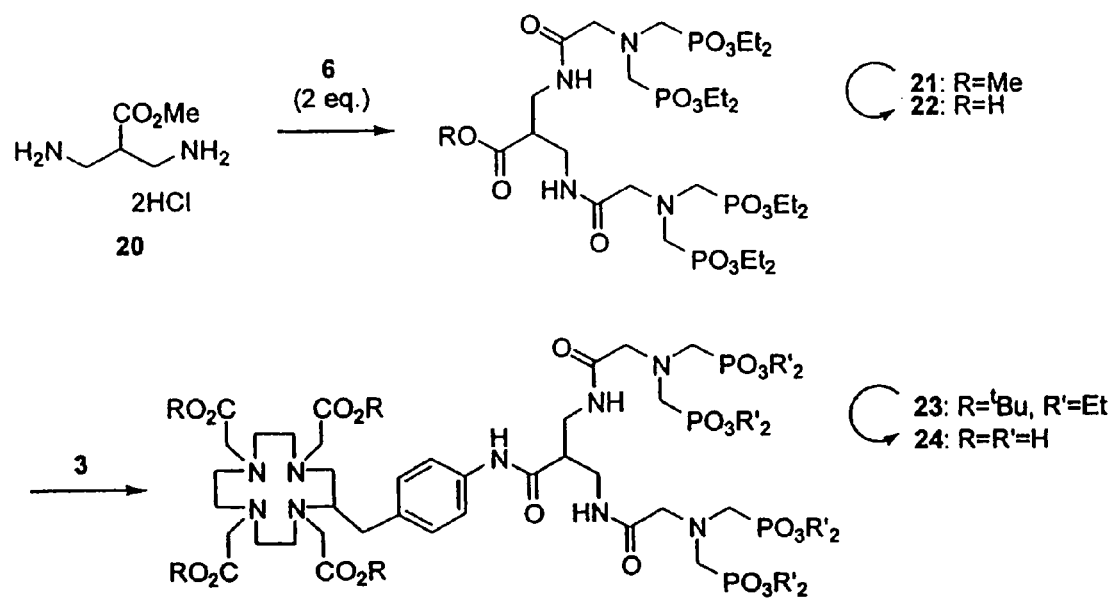

{3-[4-(3-[2-(Bis-phosphonomethyl-amino)-acetylamino]-2-{[2-(bis-phosphonomethyl-amino)-acetylamino]-methyl}-propionylamino)-benzyl]-4,7,10-tris-carboxymethyl-1,4,7,10-tetraaza-cyclododec-1-yl}-acetic acid (24, FIG. 8)

To a solution of compound 23 (25.9 mg; 12.2 µmol) in $CH_2Cl_2$ (3 mL) under nitrogen was added TMSBr (0.5 mL). The solution was stirred overnight then cooled in an ice bath. $H_2O$ (3 mL) was added and stirring continued for 30 minutes. Concentration yielded 23.9 mg of crude product. Purification by preparative HPLC on a C-18 reversed phase column eluting with $H_2O$/MeCN containing 0.1% TFA (using a gradient of 0-8% MeCN over 30 min) yielded 8.7 mg (43%) of 24 as its penta TFA salt: $^1$H NMR ($D_2O$) δ 7.37 (d, 2H), 7.17 (d, 2H), 4.47-2.48 (complex multiplet, 27H), 2.40 (t, 2H), 2.28 (t, 2H), 2.15 (m, 2H), 1.93 (m, 2H); ESI-MS 841.4 (M+H), 879.2 (M+K).

The intermediate compound 23 was prepared as follows.

a. Tetraphosphonate methyl ester 21 (FIG. 8). To a solution of bisamine 20 (51.3 mg; 0.25 mmol) and acid 6 (218 mg; 0.53 mmol) in anhydrous DMF (4 mL) was added BOP (234 mg; 0.53 mmol) followed by DIEA (0.65 mL; 3.75 mmol). The mixture was stirred, under nitrogen, at room temperature overnight, then concentrated to give 635 mg of crude material. Purification by flash chromatography ($SiO_2$; 0-10% MeOH/$CH_2Cl_2$ containing 0.1% $Et_3N$) yielded 428 mg (>100%) of 21 which still contained some HMPA impurity. This material was used in subsequent steps without further purification: $R_f=0.27$ (10% MeOH/$CH_2Cl_2$+0.1% $Et_3N$); $^1H$ NMR ($CDCl_3$) δ 7.71 (t, 2NH), 4.12 (pentet, 16H), 3.78-3.40 (m, 4H), 3.69 (s, 3H), 3.50 (s, 2H), 3.22 (m, 8H), 2.92 (m, 1H), 1.32 (t, 24H); ESI-MS 847.0 (M+H), 869.2 (M+Na).

b. Tetraphosphonate carboxylic acid 22 (FIG. 8). To a solution of methyl ester 21 (153.9 mg; 167 μmol) in MeOH (3 mL) and water (3 mL) was added 1N—NaOH (1 mL). The mixture was stirred overnight then concentrated and the crude residue dissolved in $H_2O$ (5 mL). The aqueous solution was acidified to pH-2 with 1N—HCl (1 mL) then concentrated. MeCN (5 mL) was added to the residue and the insoluble NaCl removed by filtration. Concentration of the mother liquor yielded 101 mg (67% for 2 steps) of acid 22 which was of sufficient purity to be used in subsequent experiments: $^1H$ NMR ($CDCl_3$) δ 7.78 (t, 2NH), 4.11 (multiplet, 16H), 3.80-3.35 (m, 8H), 3.48 (s, 4H), 3.17 (d, 8H), 2.83 (m, 1H), 1.31 (t, 24H); ESI-MS 833.0 (M+H), 855.2 (M+Na).

c. Compound 23 (FIG. 8). To a solution of amine 3 (82 mg; 112 μmol) and acid 22 (101.3 mg; 112 μmol) in anhydrous DMF (3 mL) was added BOP (49.5 mg; 112 μmol) followed by DIEA (293 μL; 1.68 mmol). The mixture was stirred, under nitrogen, at room temperature overnight then concentrated to give 323 mg of crude material. Purification by flash chromatography ($SiO_2$; 0-10% MeOH/$CH_2Cl_2$ containing 0.1% $Et_3N$) yielded 64 mg of 23 which was further purified by preparative HPLC on a C-18 reversed phase column, eluting with $H_2O$/MeCN containing 0.1% TFA (using a gradient of 40-64% MeCN over 30 min) to yield 25.9 mg (11%) of 23 as its penta TFA salt: $R_f=0.11$ (10% MeOH/$CH_2Cl_2$+0.2% $Et_3N$); $^1H$ NMR ($CDCl_3$) δ 7.47 (d, 2H), 7.13 (d, 2H), 4.11 (pentet, 16H), 4.00-2.28 (complex multiplet, 38H), 3.48 (s, 4H), 1.59-1.42 (4s, 36H), 1.35 (t, 24H); ESI-MS 774.9 ([M+2H]/2), 1548.5 (M+H), 1570.6 (M+Na).

EXAMPLE 6

Figure 9:
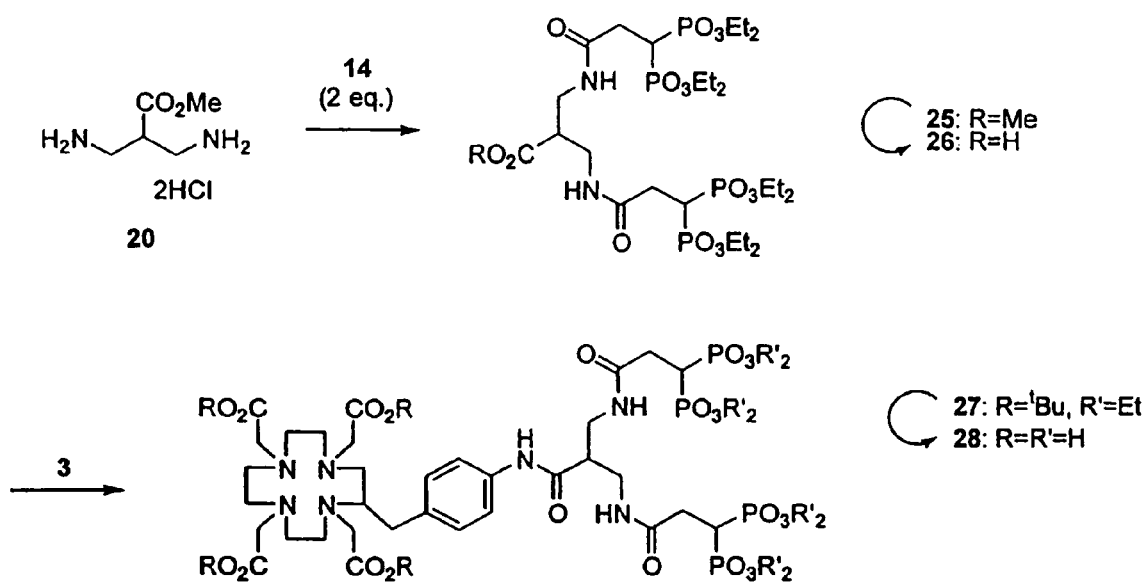

[3-(4-{3-(3,3-Bis-phosphono-propionylamino)-2-[(3, 3-bis-phosphono-propionylamino)-methyl]-propionylamino}-benzyl)-4,7,10-tris-carboxymethyl-1,4,7, 10tetraaza-cyclododec-1-yl]-acetic acid (28, FIG. 9)

To a solution of compound 27 (64 mg; 43.0 μmol) in $CH_2Cl_2$ (4 mL) under nitrogen was added TMSBr (0.5 mL). The solution was stirred overnight then cooled in an ice bath. $H_2O$ (1 mL) was added and stirring continued for 30 minutes. Concentration yielded 78.6 mg of crude product. Purification by preparative HPLC on a C-18 reversed phase column eluting with $H_2O$/MeCN containing 0.1% TFA (using a gradient of 0-20% MeCN over 30 min) yielded 26.5 mg (45%) of compound 28 as its tri TFA salt: $^1H$ NMR ($D_2O$) δ 7.43 (m, 2H), 7.28 (m, 2H), 4.27-2.35 (complex multiplet, 36H); ESI-MS: 533.8 ([M+H+Na]/2), 1042.3 (M+H), 1066.2 (M+Na).

The intermediate compound 27 was prepared as follows.

a. Tetraphosphonate methyl ester 25 (FIG. 9). To a solution of bisamine 20 (51.3 mg; 250 μmol) and acid 14 (190.4 mg; 550 μmol) in anhydrous DMF (4 mL) was added BOP (243 mg; 550 μmol) followed by DIEA (871 mL; 5 mmol). The mixture was stirred, under nitrogen, at room temperature overnight, then concentrated. The residue was dissolved in $CH_2Cl_2$ (20 mL) and washed with 1N—HCl (2×10 mL), $H_2O$ (10 mL) and saturated aqueous $NaHCO_3$ solution (10 mL). Drying ($MgSO_4$) and concentration yielded 224 mg of crude material. Purification by flash chromatography ($SiO_2$; 0-10% MeOH/$CH_2Cl_2$) yielded 96.4 mg (49%) of 25: $R_f=0.32$ (10% MeOH/$CH_2Cl_2$); $^1H$ NMR ($CDCl_3$) δ 7.53 (t, 2NH), 4.09 (m, 16H), 3.68 (m, 2H), 3.62 (s, 3H), 3.45-3.09 (m, 4H), 2.98 (m, 1H), 2.65 (dt, 4H), 1.26 (t, 24H); ESI-MS 789.0 (M+H), 811.2 (M+Na), 827.1 (M+K).

b. Tetraphosphonate carboxylic acid 26 (FIG. 9). To a solution of methyl ester 25 (95 mg; 120 μmol) in MeOH (2 mL) and $H_2O$ (1 mL) was added 1N—NaOH (150 μL). The solution was stirred at room temperature overnight then concentrated. The residue was dissolved in $H_2O$ (5 mL) then acidified to pH-2 with 1N—HCl (150 μL). The aqueous solution was extracted with 3:1 $CH_2Cl_2$: $^iPrOH$ (3×5 mL) and the combined organics dried ($Na_2SO_4$) and concentrated to give 88.1 mg (95%) of 26, which was of sufficient purity to be used in subsequent steps: $^1H$ NWR ($CD_3OD$) δ 8.19 (t, 2NH), 4.18 (pentet, 16H), 3.63-3.11 (m, 6H), 2.81 (m, 1H), 2.72 (dt, 4H), 1.33 (t, 24H); ESI-MS 775.0 (M+H), 797.2 (M+Na).

C. Compound 27 (FIG. 9). To a solution of amine 3 (83 mg; 114 μmol) and acid 26 (88 mg; 114 μmol) in anhydrous DMF (3 mL) was added BOP (50 mg; 114 μmol) followed by DIEA (200 μL; 0.57 mmol). The mixture was stirred, under nitrogen, at room temperature overnight, then concentrated to give 259 mg of crude material. Purification by flash chromatography ($SiO_2$; 0-10% MeOH/$CH_2Cl_2$) yielded 128.3 mg (79%) of 27: TLC $R_f=0.38$ (10% MeOH/$CH_2Cl_2$); $^1H$ NMR ($CDCl_3$) δ 7.54 (d, 2H), 7.15 (dd, 2H), 4.14 (m, 16H), 3.65-1.70 (complex multiplet, 36H), 1.50-1.38 (4s, 36H), 1.33 (t, 24H); ESI-MS 746.0 ([M+2H]/2), 756.9 ([M+H+Na]/2), 768.0 ([M+2Na]/2), 1490.4 (M+H), 1512.5 (M+Na).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A composition comprising:
a) a compound of formula (I):

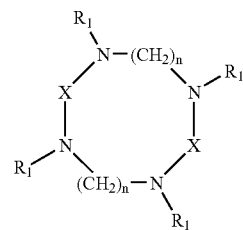

wherein:
each $R_1$ is independently hydrogen or ($C_1$-$C_4$)alkyl, optionally substituted with carboxy;

each X is independently $(CH_2)_n$ or

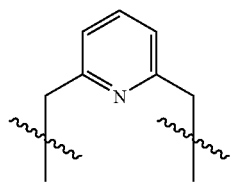

and each n is independently 2, 3, or 4;
wherein the compound of formula I is substituted on one or more carbons other than a carbon of $R_1$ with one or more groups $-Y(PO_3H_2)_m$; wherein Y is a linker group; and m is 1, 2, 3, 4, 5, or 6; or a pharmaceutically acceptable salt thereof;
b) a detectable or therapeutic radionuclide; and
c) a radioprotectant.

2. The composition of claim 1, which comprises a detectable radionuclide.

3. The composition of claim 2, wherein the detectable radionuclide is Technetium-99m, Ruthenium-97, Indium-111, Gallium-67 or -68 or Lead-203.

4. The composition of claim 1, which comprises a therapeutic radionuclide.

5. The composition of claim 4, wherein the therapeutic radionuclide is Holmium-166, Yttrium-90, Samarium-153, or Gadolinium-159.

6. The composition of claim 1, wherein the radioprotectant is an anti-oxidant.

7. The composition of claim 1, wherein the radioprotectant is ascorbic acid, gentisic acid, nicotinic acid, ascorbyl palmitate, $HOP(O)H_2$, monthioglycerol, sodium formaldehyde sulfoxylate, $Na_2S_2O_5$, $Na_2S_2O_3$, or $SO_2$.

8. The composition of claim 1, wherein the radioprotect is a reducing agent combined with BHA, BHT, pyrogallate or tocopherol.

9. The composition of claim 1, wherein the radioprotectant is ascorbic acid.

10. The composition of claim 9, wherein the ascorbic acid is present in the amount of about 35-75 mg/mL of liquid composition.

11. The composition of claim 1, wherein the composition is buffered to a pH of 7-8.

12. The composition of claim 1 further comprising a pharmaceutically acceptable carrier.

13. A method of preparing the composition of claim 1 comprising admixing a compound of formula (I), a radionuclide and a radioprotectant.

14. The method of claim 13, further comprising admixing a pharmaceutically acceptable carrier.

15. A kit comprising the composition of claim 1.

16. The kit of claim 15 further comprising a pharmaceutically acceptable carrier.

* * * * *

UNITED STATES PATENT AND TRADEMARK OFFICE
CERTIFICATE OF CORRECTION

PATENT NO. : 7,385,042 B2                                                Page 1 of 1
APPLICATION NO. : 11/486338
DATED : June 10, 2008
INVENTOR(S) : Fritzberg It is certified that error appears in the above-identified patent and that said Letters Patent is hereby corrected as shown below:

In column 7, line 59, delete "R" and insert -- $R^1$ --, therefor.

In column 12, line 3, delete "RX" and insert -- $R_1$ --, therefor.

In column 12, line 60, delete "R," and insert -- $R_1$ --, therefor.

In column 16, line 22, delete "adriamnycin," and insert -- adriamycin, --, therefor.

In column 18, line 66, delete "stern" and insert -- stem --, therefor.

In column 24, line 28, delete "pH-2" and insert -- pH~2 --, therefor.

In column 25, line 30, delete "6. see" and insert -- 6, see --, therefor.

In column 25, line 31, delete "1990. 30.855" and insert -- 1990, 30, 855 --, therefor.

Signed and Sealed this

Fourteenth Day of October, 2008

JON W. DUDAS
*Director of the United States Patent and Trademark Office*